(12) United States Patent
Buchmann et al.

(10) Patent No.: US 7,449,459 B2
(45) Date of Patent: Nov. 11, 2008

(54) INHIBITORS OF SOLUBLE ADENYLATE CYCLASE

(75) Inventors: Bernd Buchmann, Hohen Neuendorf (DE); Dirk Kosemund, Erfurt (DE); Bernd Menzenbach, Jena (DE); Martin Fritsch, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 0 days.

(21) Appl. No.: 11/727,167

(22) Filed: Mar. 23, 2007

(65) Prior Publication Data

US 2007/0232605 A1 Oct. 4, 2007

Related U.S. Application Data

(60) Provisional application No. 60/788,075, filed on Apr. 3, 2006.

(30) Foreign Application Priority Data

Mar. 20, 2006 (DE) .................. 10 2006 014 324

(51) Int. Cl.
*A61K 31/535* (2006.01)
*A61K 31/445* (2006.01)
*A61K 31/44* (2006.01)
*A61K 31/40* (2006.01)
*C07D 413/00* (2006.01)
*C07D 401/00* (2006.01)
*C07D 209/02* (2006.01)
*C07D 209/04* (2006.01)

(52) U.S. Cl. .................. 514/232.8; 514/323; 514/337; 514/414; 514/419; 544/143; 546/201; 546/277.4; 548/465; 548/466; 548/469; 548/495

(58) Field of Classification Search ............. 514/232.8, 514/337, 414, 323, 419; 544/143; 546/201; 546/277.4; 548/466, 465, 495, 469
See application file for complete search history.

(56) References Cited

U.S. PATENT DOCUMENTS

2006/0074084 A1   4/2006   Nguyen et al.
2006/0128722 A1   6/2006   Hermkens et al.

FOREIGN PATENT DOCUMENTS

WO   WO 2004/041782 A   5/2004
WO   WO 2006/032541 A   3/2006

*Primary Examiner*—Kamal Saeed
*Assistant Examiner*—Kristin Bianchi
(74) *Attorney, Agent, or Firm*—Millen, White, Zelano, Branigan, P.C.

(57) ABSTRACT

The invention relates to compounds of general formula I as well as the production and use thereof as a medication.

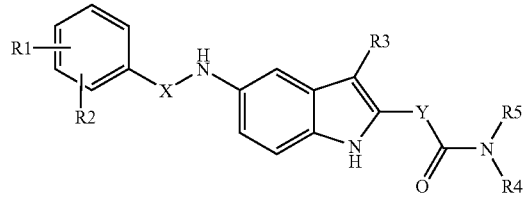

22 Claims, No Drawings

INHIBITORS OF SOLUBLE ADENYLATE CYCLASE

This application claims the benefit of the filing date of U.S. Provisional Application Ser. No. 60/788,075 filed Apr. 3, 2006.

This invention relates to inhibitors of soluble adenylate cyclase, its production as well as its use for the production of a pharmaceutical agent for contraception.

There are currently a number of modern contraceptive methods available for women; for male birth control, however, only very few methods are available (condom and sterilization). The development of new reliable agents for male birth control is absolutely necessary. In this connection, infertility produced by a "male pill" should be completely reversible and just as effective as the existing methods that are available to women. The infertility should set in relatively quickly and last as long as possible. Such contraceptive methods should not have any side effects; in addition to hormonal preparations, these can also be non-hormonal preparations in this connection. A possible starting point is the regulation of the activity of an enzyme, which plays an important role in the fertilization of an ovocyte, the soluble adenylate cyclase (sAC). This enzyme is expressed mainly in the testicular stem cells and is present in mature sperm.

In 1999, the authors Levin and Buck (Proc. Natl. Acad. Sci. USA 96 (1): 79-84) were able to purify and to clone an isoform of the sAC from the testes of rats.

The recombinant enzyme of rats can be stimulated by bicarbonate. By means of antibodies, it was possible to demonstrate that the catalytic domain of the enzyme is located in the testes, sperm, kidneys and the choroid plexus. These disclosures are the subject matter of the application WO01/85753, which was granted in the U.S. (U.S. Pat. No. 6,544,768).

In WO01/21829 (Conti et al.), isolated polynucleotide sequences that code for the human isoform of sAC, isolated sAC polypeptides and test systems are claimed with whose help substances can be identified that inhibit the activity of sAC. The possibility of using these substances to reduce the number of motile sperm cells in a reversible manner as well as their use as agents for male birth control are disclosed.

The John Herr group showed the isolation and characterization of the human isoform of sAC from sperm. In WO 02/20745, in addition to nucleic acids, the test systems that also code for sAC are claimed, with whose aid substances can be identified that modulate the expression or the activity of the human sAC. Such compounds could selectively inhibit, for example, the activity of sAC; this had the result that the sperm cells lose the ability to fertilize an ovocyte. These inhibitors of sAC therefore could be used as pharmaceutical agents for non-hormonal contraception.

The already known inhibitors of sAC indicate specific problems, however: catechol estrogens (T. Braun, Proc Soc Exp Biol Med 1990, 194(1): 58ff) and gossypol (K. L. Olgiati, Arch Biochem Biophys 1984, 231(2): 411ff) are inherently toxic, while adenosine analogs inhibit with only very weak action (M. A. Brown and E. R. Casillas, J Androl 1984, 5:361ff). The inhibitors ($IC_{50} \leq 10$ µmol) of the recombinant human sAC, which are described by Zippin et al. (J. H. Zippin et al. *J Cell Biol* 2004, 164(4): 527ff), are somewhat more potent.

To be able to make an agent for male birth control available, there is an increasing need for substances that are reversible, quick and successfully result in infertility.

This object is achieved by the provision of the compounds of general formula I

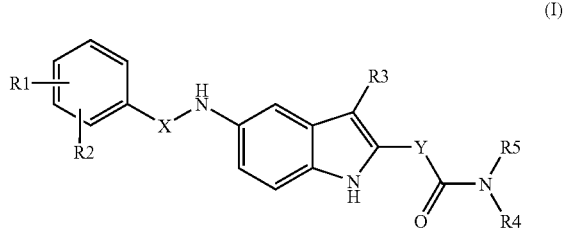

(I)

whereby $R^1$ means hydrogen, halogen, $CF_3$, $C_3$-$C_6$-cycloalkyl, which optionally is polysaturated and optionally is polysubstituted, or the group $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, $C_1$-$C_6$-aryl-$C_1$-$C_6$-alkyl or $CF_3$, in which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl optionally can be interrupted in one or more places, in the same way or differently, by oxygen, sulfur or nitrogen, or the group sulfonyl-$C_1$-$C_6$-alkyl, sulfonamide, or cyano, $R^2$ means halogen, $CF_3$, $C_3$-$C_6$-cycloalkyl, which optionally is polysaturated and optionally is polysubstituted, or the group $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, $C_1$-$C_6$-aryl-$C_1$-$C_6$-alkyl or $CF_3$, in which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl optionally can be interrupted in one or more places, in the same way or differently, by oxygen, sulfur or nitrogen, or the group sulfonyl-$C_1$-$C_6$-alkyl, sulfonamide, or cyano, $R^3$ means $C_6$-$C_{12}$-aryl, which optionally can be substituted in one or more places, in the same way or differently, with halogen, with $C_1$-$C_6$-alkyl or $C_1$-$C_6$-acyl, which optionally can be substituted in one or more places, or can be substituted with $C_1$-$C_6$-alkoxy, hydroxy, cyano, $CO_2$—($C_1$-$C_6$-alkyl), N—($C_1$-$C_6$-alkyl)$_2$, CO—$NR^4R^5$ or with $CF_3$;

$C_5$-$C_{12}$-heteroaryl, which optionally can be substituted in one or more places, in the same way or differently, with halogen, with $C_1$-$C_6$-alkyl, $C_1$-$C_6$-acyl, $C_1$-$C_6$-alkoxy, hydroxy, cyano, $CO_2$—($C_1$-$C_6$-alkyl), N—($C_1$-$C_6$-alkyl)$_2$, CO—$NR^4R^5$ or with $CF_3$; or $C_3$-$C_6$-cycloalkyl, which optionally can be substituted in one or more places, in the same way or differently, with halogen, $CF_3$, hydroxy, cyano, $CO_2$—($C_1$-$C_6$-alkyl), $C_1$-$C_6$-alkyl, $C_1$-$C_6$-acyl, N—($C_1$-$C_6$-alkyl)$_2$, CO—$NR^4R^5$ or $C_1$-$C_6$-alkoxy, $R^4$ means hydrogen, $C_3$-$C_6$-cycloalkyl, which optionally is substituted in one or more places, in the same way or differently, with $C_1$-$C_6$-alkyl, $C_1$-$C_6$-acyl, $C_1$-$C_6$-alkoxy or $CF_3$;

$C_6$-$C_{12}$-aryl, which optionally is substituted in one or more places, in the same way or differently, with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano; or $C_5$-$C_{12}$-heteroaryl, which optionally is substituted in one or more places, in the same way or differently, with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano; or $C_1$-$C_6$-alkyl, which can be substituted in any way desired, $R^5$ means hydrogen, $C_1$-$C_6$-alkyl-$C_3$-$C_6$-cycloalkyl, which optionally is substituted in one or more places, in the same way or differently, with $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, with $C_1$-$C_6$-alkyl, $C_1$-$C_6$-acyl, $C_1$-$C_6$-alkoxy or $CF_3$;

$C_6$-$C_{12}$-aryl, which optionally is substituted in one or more places, in the same way or differently, with halogen, with $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano; or $C_5$-$C_{12}$-heteroaryl, which optionally is substituted in one or more places, in the same way or differently, with halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano; or $C_1$-$C_6$-alkyl, which can be substituted in any way desired, $R^4$ and $R^5$ together form a 5 to 8-membered ring, which can contain additional heteroatoms, and X means the groups sulfonyl, $(CH_2)_n$ or carbonyl, Y means —$(CH_2)_n$— or —CH=CH—, n means 1-4, as well as the isomers, diastereomers, enantiomers and salts thereof that overcome the known disadvantages and exhibit improved properties, i.e., good effectiveness, good solubility and stability.

The compounds according to the invention inhibit the soluble adenylate cyclase and thus prevent sperm capacitation and thus are used for male birth control.

Alkyl is defined in each case as a straight-chain or branched alkyl radical, such as, for example, methyl, ethyl, propyl, isopropyl, butyl, isobutyl, sec-butyl, tert-butyl, pentyl, iso-pentyl and hexyl.

Alkoxy is defined in each case as a straight-chain or branched alkoxy radical, such as, for example, methoxy, ethoxy, n-propoxy, iso-propoxy, n-butoxy, sec-butoxy, iso-butoxy, tert-butyloxy, pentoxy, iso-pentoxy and hexoxy.

Acyl is defined in each case as a straight-chain or branched radical, such as, for example, formyl, acetyl, propionyl, butyroyl, iso-butyroyl, valeroyl and benzoyl.

Cycloalkyls are defined as monocyclic alkyl rings such as cyclopropyl, cyclobutyl, cyclopentyl, and cyclohexyl.

Instead of the carbon atoms, the cycloalkyl radicals can contain one or more heteroatoms, such as oxygen, sulfur and/or nitrogen. Preferred are those heterocycloalkyls with 3 to 6 ring atoms. The ring systems, in which optionally one or more possible double bonds can be contained in the ring, are defined as, for example, cycloalkenyls, such as cyclopropenyl, cyclobutenyl, cyclopentenyl, cyclopentadienyl, cyclohexenyl, or cycloheptenyl, whereby the linkage both to the double bond and to the single bonds can be carried out.

Halogen is defined as fluorine, chlorine, bromine or iodine in each case.

In each case, the aryl radical comprises 6-12 carbon atoms and can be, for example, benzocondensed. For example, the following can be mentioned: phenyl, tropyl, cyclooctadienyl, indenyl, naphthyl, biphenyl, florenyl, anthracenyl, etc.

The heteroaryl radical comprises 5-16 ring atoms in each case and instead of the carbon can contain one or more heteroatoms that are the same or different, such as oxygen, sulfur or nitrogen, in the ring, and can be monocyclic, bicyclic or tricyclic, and in addition can be benzocondensed in each case.

For example, there can be mentioned:

Thienyl, furanyl, pyrrolyl, oxazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzooxazolyl, benzimidazolyl, indazolyl, indolyl, isoindolyl, etc.; or pyridazinyl, pyrimidinyl, pyrazinyl, triazinyl, etc., and benzo derivatives thereof, such as, e.g., quinolyl, isoquinolyl, etc.; or azocinyl, indolizinyl, purinyl, etc., and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, oxepinyl, etc.

The heteroaryl radical can be benzocondensed in each case. For example, thiophene, furan, oxazole, thiazole, imidazole, pyrazole and benzo derivatives thereof can be mentioned as 5-ring heteroaromatic compounds, and pyridine, pyrimidine, triazine, quinoline, isoquinoline and benzo derivatives can be mentioned as 6-ring heteroaromatic compounds.

Heteroatoms are defined as oxygen, nitrogen or sulfur atoms.

If an acid group is included, the physiologically compatible salts of organic and inorganic bases, such as, for example, the readily soluble alkali and alkaline-earth salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol, are suitable as salts.

If a basic group is included, the physiologically compatible salts of organic and inorganic acids, such as hydrochloric acid, sulfuric acid, phosphoric acid, citric acid, tartaric acid, i.a., are suitable.

Those compounds of general formula (I), whereby $R^1$ means hydrogen, halogen, $CF_3$, $C_3$-$C_6$-cycloalkyl, or the group $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, $C_1$-$C_6$-aryl-$C_1$-$C_6$-alkyl or $CF_3$, in which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl optionally can be interrupted in one or more places, in the same way or differently, by oxygen, sulfur or nitrogen, or the group sulfonyl-$C_1$-$C_6$-alkyl, sulfonamide, or cyano, $R^2$ means halogen, $CF_3$, or $C_3$-$C_6$-cycloalkyl, or the group $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, $C_1$-$C_6$-aryl-$C_1$-$C_6$-alkyl or $CF_3$, in which $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl or $C_1$-$C_6$-aryl-$C_1$-$C_6$-alkyl optionally can be interrupted in one or more places, in the same way or differently, by oxygen, sulfur or nitrogen, or the group sulfonyl-$C_1$-$C_6$-alkyl, sulfonamide, or cyano, $R^3$ means $C_6$-$C_{12}$-aryl, which optionally can be substituted in one or more places, in the same way or differently, with halogen, with $C_1$-$C_6$-alkyl, $C_1$-$C_3$-acyl, $C_1$-$C_3$- alkoxy, cyano, hydroxy, N—$(CH_3)_2$, $CO_2$—($C_1$-$C_3$-alkyl), CO—$NR^4R^5$ or with $CF_3$;

$C_5$-$C_{12}$-heteroaryl, which optionally can be substituted in one or more places, in the same way or differently, with chlorine and/or fluorine, with $C_1$-$C_6$-alkyl, $C_1$-$C_3$-acyl, $C_1$-$C_3$-alkoxy, cyano, hydroxy, N—$(CH_3)_2$, $CO_2$—($C_1$-$C_3$-alkyl), CO—$NR^4R^5$ or with $CF_3$;

$C_3$-$C_6$-cycloalkyl, which optionally can be substituted in one or more places, in the same way or differently, with chlorine and/or fluorine, $CF_3$, cyano, $C_1$-$C_3$-alkyl, $C_1$-$C_3$-acyl, hydroxy, N—$(CH_3)_2$, $CO_2$—($C_1$-$C_3$-alkyl), CO—$NR^4R^5$ or $C_1$-$C_3$-alkoxy, $R^4$ means hydrogen, $C_3$-$C_6$-cycloalkyl, which optionally is substituted in one or more places, in the same way or differently, with $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_5$-$C_{12}$-heteroaryl, which optionally is substituted in one or more places, in the same way or differently, with halogen, with $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, which can be substituted in any way desired, $R^5$ means hydrogen, $C_1$-$C_6$-alkyl-$C_3$-$C_6$-cycloalkyl, which optionally is substituted in one or more places, in the same way or differently, with $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, with $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_5$-$C_{12}$-heteroaryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, which can be substituted in any way desired, $R^4$ and $R^5$ together form a 5- to 8-membered ring, which can contain additional heteroatoms, and X means the groups sulfonyl, $(CH_2)_n$ or carbonyl, Y means —$(CH_2)_n$— or —CH=CH—, n means 1-2, as well as the isomers, diastereomers, enantiomers and salts thereof, are especially preferred.

Those compounds of general formula I, whereby $R^1$ means hydrogen, $R^2$ means $C_3$-$C_6$-cycloalkyl, $C_1$-$C_6$-alkyl, $CF_3$, cyano, bromine, or the group —$OCF_3$, or —$SO_2$—$CH_3$, $R^3$ means $C_6$-$C_{12}$-aryl, which optionally can be substituted in one or more places, in the same way or differently, with halogen, $C_1$-$C_6$-alkyl, $C_1$-$C_3$-acyl, $C_1$-$C_3$-alkoxy, cyano, hydroxy, N—$(CH_3)_2$, $CO_2$—($C_1$-$C_3$-alkyl), CO—$NR^4R^5$ or $CF_3$;

$C_5$-$C_{12}$-heteroaryl, which optionally can be substituted in one or more places, in the same way or differently, with chlorine and/or fluorine, with $C_1$-$C_6$-alkyl, $C_1$-$C_3$-acyl, $C_1$-$C_3$-alkoxy, cyano, hydroxy, N—$(CH_3)_2$, $CO_2$—($C_1$-$C_3$-alkyl), CO—$NR^4R^5$ or with $CF_3$;

$C_3$-$C_6$-cycloalkyl, which optionally can be substituted in one or more places, in the same way or differently, with chlorine and/or fluorine, $CF_3$, cyano, $C_1$-$C_3$-alkyl, $C_1$-$C_3$-acyl, hydroxy, N—$(CH_3)_2$, $CO_2$—($C_1$-$C_3$-alkyl), CO—$NR^4R^5$ or $C_1$-$C_3$-alkoxy, $R^4$ means hydrogen, $R^5$ means hydrogen, $C_1$-$C_6$-alkyl-$C_3$-$C_6$-cycloalkyl, which optionally is substituted in one or more places, in the same way or differently, with $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, with $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_5$-$C_{12}$-heteroaryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, which can be substituted in any way desired, X means the group sulfonyl, Y means —$(CH_2)_n$— or —CH=CH—, n means 1-2, as well as the isomers, diastereomers, enantiomers and salts thereof, are also preferred.

Those compounds of general formula I, whereby $R^1$ means hydrogen, $R^2$ means $C_3$-$C_6$-cycloalkyl, $C_1$-$C_6$-alkyl, $CF_3$, cyano, bromine, or the group —$OCF_3$, or —$SO_2$—$CH_3$ and is in para-position, $R^3$ means $C_6$-$C_{12}$-aryl, which optionally can be substituted in one or two places, in the same way or differently, with halogen, $C_1$-$C_3$-alkyl, acetyl, methoxy, ethoxy, cyano, hydroxy, N—$(CH_3)_2$, $CO_2$—($C_1$-$C_3$-alkyl), CO—$NHR^5$ or $CF_3$;

$C_5$-$C_{12}$-heteroaryl, which optionally can be substituted in one or two places, in the same way or differently, with chlorine and/or fluorine, with $C_1$-$C_3$-alkyl, acetyl, methoxy, ethoxy, cyano, hydroxy, N—$(CH_3)_2$, $CO_2$—($C_1$-$C_3$-alkyl), CO—$NHR^5$ or with $CF_3$; or $C_3$-$C_6$-cycloalkyl, $R^4$ means hydrogen, $R^5$ means hydrogen, or $C_1$-$C_6$-alkyl-$C_3$-$C_6$-cycloalkyl, which optionally is substituted in one or more places, in the same way or differently, with $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, with $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_5$-$C_{12}$-heteroaryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, which can be substituted in any way desired, X means the group sulfonyl, Y means —$(CH_2)_n$— or —CH=CH—, n means 1-2, as well as the isomers, diastereomers, enantiomers and salts thereof, are also preferred.

Those compounds of general formula I, whereby $R^1$ means hydrogen, $R^2$ means tert-butyl, iso-propyl, iso-butyl, sec-butyl, cyano, bromine, or the group —O—$CF_3$, or —$SO_2$—$CH_3$ and is in para-position, $R^3$ means the group

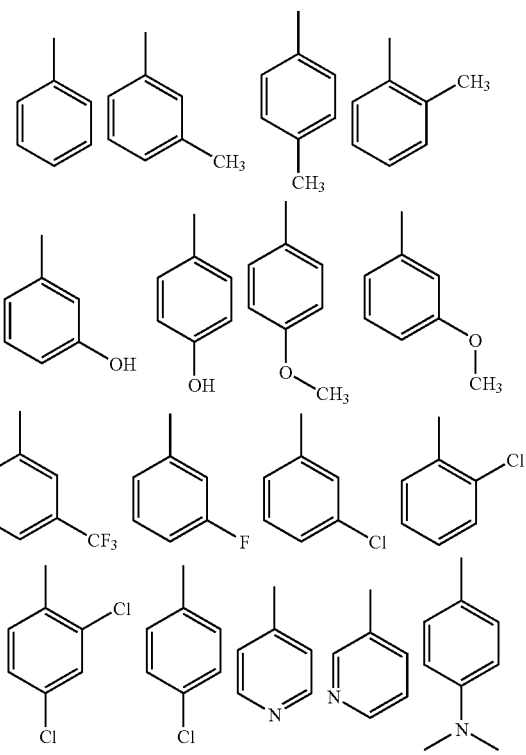

$R^4$ means hydrogen, $R^5$ means hydrogen or the group —$(CH_2)_n$—N—$(CH_3)_2$, —$(CH_2)_2$—$CH_3$, —$(CH_2)_2$—NH—$COCH_3$, —$(CH_2)$—$CHCH_3$—OH, —$(CH_2)_2$—O—$CH_3$, —$(CH_2)_2$—OH, or —$CHCH_3$—$CH_2$—OH,

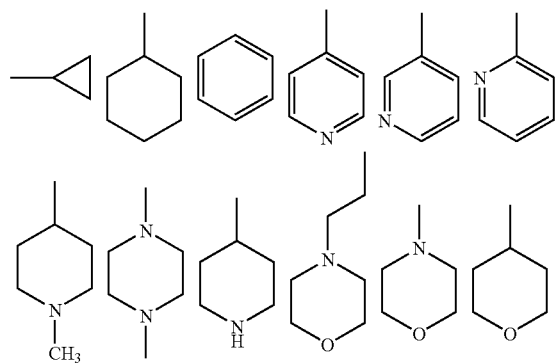

-continued

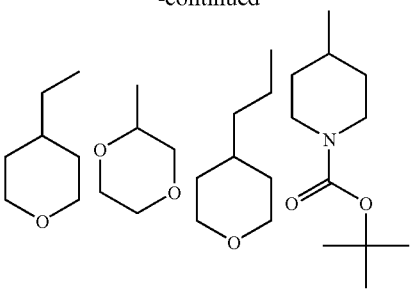

X means the sulfonyl group,

Y means —$(CH_2)_n$— or —CH=CH—, n means 1-2, as well as the isomers, diastereomers, enantiomers and salts thereof, are also preferred.

Those compounds of general formula I, whereby $R^1$ means hydrogen, $R^2$ means tert-butyl, iso-propyl, iso-butyl, sec-butyl, cyano, bromine, or the group —O—$CF_3$, or —$SO_2$—$CH_3$ and is in para-position, $R^3$ means the group

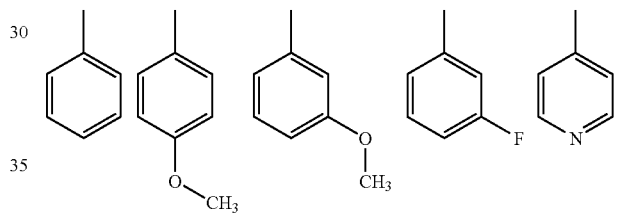

$R^4$ means hydrogen, $R^5$ means hydrogen or the group —$(CH_2)$—$CHCH_3$—OH, —$(CH_2)_2$—O—$CH_3$, or —$CHCH_3$—$CH_2$—OH,

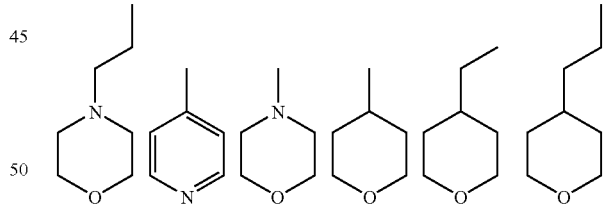

X means the sulfonyl group,

Y means —$(CH_2)_n$— or —CH=CH—, and n means 1-2 as well as the isomers, diastereomers, enantiomers and salts thereof, are also preferred.

The following compounds corresponding to this invention are quite especially preferred:

1. (E)-3-[5-(4-tert-Butyl-phenylsulfonylamino)-3-phenyl-1H-indol-2-yl]-N-(tetrahydro-pyran-4-yl)-acrylic acid amide 2. (E)-3-[5-(4-tert-Butyl-phenylsulfonylamino)-3-phenyl-1H-indol-2-yl]-N-(2-morpholin-4-yl-ethyl)-acrylic acid amide 3. (±)-(E)-3-[5-(4-tert-Butyl-phenylsulfonylamino)-3-phenyl-1H-indol-2-yl]-N-(2-hydroxy-1-methyl-ethyl)-acrylic acid amide
4. (±)-(E)-3-[5-(4-tert-Butyl-phenylsulfonylamino)-3-phenyl-1H-indol-2-yl]-N-(2-hydroxy-propyl)-acrylic acid amide
5. 3-[5-(4-tert-Butyl-phenylsulfonylamino)-3-phenyl-1H-indol-2-yl]-N-(2-morpholin-4-yl-ethyl)-propionic acid amide
6. (E)-3-[5-(4-tert-Butyl-phenylsulfonylamino)-3-(3-fluorophenyl)-1H-indol-2-yl]-N-(tetrahydro-pyran-4-yl)-acrylic acid amide
7. (E)-3-[5-(4-tert-Butyl-phenylsulfonylamino)-3-(3-fluorophenyl)-1H-indol-2-yl]-N-(2-morpholin-4-yl-ethyl)-acrylic acid amide
8. (E)-3-[5-(4-tert-Butyl-phenylsulfonylamino)-3-(3-methoxy-phenyl)-1H-indol-2-yl]-N-(tetrahydro-pyran-4-yl)-acrylic acid amide
9. (E)-3-[5-(4-tert-Butyl-phenylsulfonylamino)-3-(3-methoxy-phenyl)-1H-indol-2-yl]-N-(2-morpholin-4-yl-ethyl)-acrylic acid amide
10. (E)-3-[5-(4-tert-Butyl-phenylsulfonylamino)-3-(3-fluorophenyl)-1H-indol-2-yl]-N-(pyridin-4-yl)-acrylic acid amide
11. (E)-3-[5-(4-tert-Butyl-phenylsulfonylamino)-3-(3-methoxy-phenyl)-1H-indol-2-yl]-N-(pyridin-4-yl)-acrylic acid amide In addition, the invention relates to a process for the production of the compounds of general formula I according to the invention, which is characterized in that a compound of formula II

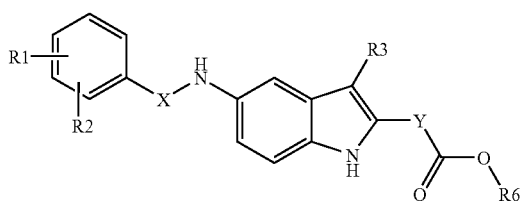
(II)

in which $R^1$, $R^2$, $R^3$, X and Y have the above-indicated meanings and $R^6$ can be a hydrogen or a $C_1$-$C_6$-alkyl radical, and is preferably hydrogen, the methyl or ethyl radical, is reacted with an amine of general formula III

(III)

in which $R^4$ and $R^5$ have the above-indicated meaning, according to the methods that are known to one skilled in the art, and/or optionally required protective groups are then cleaved and/or optionally present double bonds are hydrogenated.

For the case that $R^6$ is equal to hydrogen, the reaction first can be carried out by activating the acid function; in this case, for example, first the carboxylic acid of general formula II is converted into the mixed anhydride first in the presence of a tertiary amine, such as, for example, triethylamine, with isobutyl chloroformate. The reaction of the mixed anhydride with the alkali salt of the corresponding amine is carried out in an inert solvent or solvent mixture, such as, for example, tetrahydrofuran, dimethoxyethane, dimethylformamide, hexamethylphosphoric acid triamide, at temperatures of between −30° C. and +60° C., preferably at 0° C. to 30° C.

Another possibility consists in activating the carboxylic acid of general formula II by reagents, such as, for example, HOBt or HATU. The reaction of the acid is carried out with, e.g., HATU in an inert solvent, such as, for example, DMF in the presence of the corresponding amine of general formula III and a tertiary amine, such as, for example, ethyldiisopropylamine at temperatures of between −50 and +60° C., preferably at 0° C. to 30° C.

For the case that $R^6$ is equal to $C_1$-$C_6$-alkyl, for example, a direct amidolysis of the ester with the corresponding amine optionally also can be performed with the aid of aluminum trialkyl reagents, preferably aluminum trimethyl.

The compounds of general formula II that are used as starting materials can be produced, for example, in which in a way that is known in the art, the nitro group in the known indol esters IV

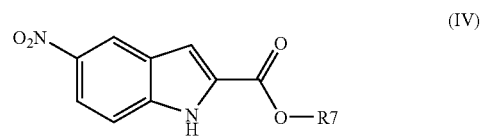
(IV)

in which $R^7$ is a $C_1$-$C_6$-alkyl radical, preferably a methyl or ethyl radical, is reduced in a hydrogen atmosphere or a hydrogen source, such as, for example, ammonium formate, in the presence of a Pd catalyst first to the amino function, and then this amine is reacted with a halide of general formula V

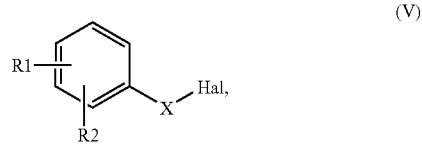
(V)

in which $R^1$, $R^2$ and X have the above-indicated meanings and Hal stands for a halogen, preferably chloride or bromide, in the presence of a base, such as, for example, pyridine, diisopropylethylamine, triethylamine or potassium carbonate, to form the compounds of general formula VI

(VI)

The esters of general formula VI are then halogenated in the 3-position, for example, by means of iodine, NBI, NBS or else $CuBr_2$ and then are converted in a Pd-catalyzed reaction with boronic acid derivatives of general formula VII

(VII)

whereby R³ has the above-indicated meaning, and subsequent reduction with, for example, diisobutylaluminium hydride into the alcohols of general formula VIII

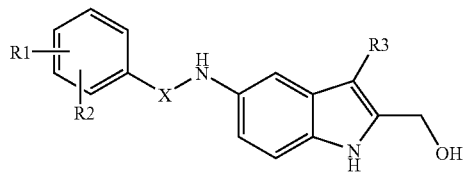
(VIII)

whereby R¹, R², R³, R⁷ and X have the above-indicated meanings.

The conversion of alcohols VIII into the compounds of general formula II is carried out either a) by converting the alcohol into a leaving group by, for example, reaction with PBr₃, thionyl chloride, tosyl chloride or mesyl chloride or CBr₄/PPh₃ and subsequent reaction with cyanide. The thus obtained cyanides can either be saponified to form the corresponding carboxylic acids and optionally then are esterified with R⁶—OH according to the methods that are known to one skilled in the art, or alternatively, the corresponding carboxylic acids could also be obtained by a reduction with, e.g., diisobutyl aluminum hydride, hydrolysis followed by an oxidation with, e.g., Jones reagent, or b) by manganese dioxide oxidation of alcohols followed by a Horner-Wittig reaction of the aldehydes that are produced with reagents, such as, for example,

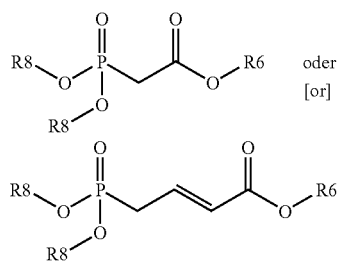

oder
[or]

in which R⁶ has the above-indicated meaning but is not equal to hydrogen, and R⁸ means the same as methyl, ethyl or trifluoroethyl, optionally followed by a hydrogenation in a hydrogen atmosphere in the presence of a Pd catalyst and optionally then the obtained esters are saponified according to the methods that are known to one skilled in the art, or c) by reduction of the cyanides that are obtained under a) with, e.g., diisobutyl aluminum hydride and hydrolysis followed by a Horner-Wittig reaction of the aldehydes that are produced with reagents, such as, for example,

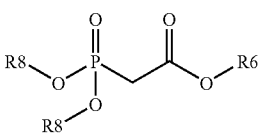

whereby R⁶ and R⁸ have the above-indicated meanings, but R⁶ is not equal to hydrogen, followed by a hydrogenation in a hydrogen atmosphere in the presence of a Pd catalyst, and optionally then the esters that are obtained are saponified according to the methods that are known to one skilled in the art.

The compounds according to the invention inhibit the soluble adenylate cyclase, upon which their action is based, for example, in the case of male birth control.

Adenylate cyclases are the effector molecules for one of the most used signal transduction methods; they synthesize the second messenger molecule of cyclic adenosine monophosphate (cAMP) from adenosine triphosphate (ATP) with cleavage of pyrophosphate (PP). cAMP mediates numerous cellular responses for a number of neurotransmitters and hormones. The soluble, sperm-specific adenylate cyclase (sAC, human mRNA sequence (gene bank) NM_018417, human gene ADCY X) is one of ten described adenylate cyclases in the human genome. In this case, sAC shows several specific properties that are distinguished from the other adenylate cyclases. In contrast to all other adenylate cyclases, sAC is stimulated by the concentration of bicarbonate in the medium that surrounds it and not by G-proteins. sAC does not have any transmembrane regions in its amino acid sequence; it cannot be inhibited by forskolin, can be stimulated much more strongly by manganese than by magnesium, and shows only low sequence homologies to the other adenylate cyclases (≦26% identity of the catalytic domains I and II of sAC with other adenylate cyclases on the amino acid plane).

Specific, manganese-dependent activity of sAC was first described by T. Braun et al. (1975, PNAS 73:1097ff) in rat testes and sperm. N. Okamura et al. (1985, J. Biol. Chem 260(17): 9699ff) showed that the substance that stimulates the activity of sAC in the pig seminal fluid is bicarbonate. It could also be shown that only in the rat testis and sperm, but not in other tissues, AC activity that can be stimulated by bicarbonate can be detected. sAC was purified from the rat testis by the Buck and Levin group and sequenced for the first time (J. Buck et al. 1999 PNAS 96:79ff, WO 01/85753). The properties that are to be expected (e.g., the ability to stimulate bicarbonate and magnesium) were confirmed in recombinantly-expressed proteins (Y. Chen et al. 2000 Science 289: 625ff).

Data regarding the distribution of sAC mRNA and the sAC activity that can be stimulated by bicarbonate can indicate a testis- and sperm-specific expression of the enzyme (M. L. Sinclair et al. 2000 Mol Reprod Develop 56:6ff; N. Okamura et al. 1985, J. Biol. Chem 260(17):9699 ff; J. Buck et al. 1999 PNAS 96:79ff). In this case, in the testicles, sAC mRNA is expressed only in later stages of the gametes that develop into sperm, but not in somatic cells (M. L. Sinclair et al. 2000 Mol Reprod Develop 56:6ff).

Regarding the function of sAC in sperm in mammals, there are a number of pharmacological studies. Before sperm penetrate the zona pellucida of the egg, so as to subsequently merge with the oolemma of the egg, they must be prepared for this functionality. This process, the sperm capacitation, is quite well studied. A capacitated sperm is distinguished by an altered pattern of movement and by the ability to go through the process of acrosomal reaction by a suitable stimulus (a release of lytic enzymes that are presumably used in the penetration of the zona pellucida by the sperm). The sperm capacitation is carried out in vivo and in vitro, i.a., based on an elevated bicarbonate concentration in the medium (P. E. Visconti & G. S. Kopf (1998) Biol Reprod 59:1ff; E. de Lamirande et al. 1997 Mol Hum Reprod 3(3):175ff). The sperm capacitation can also be stimulated by the addition of suitable membrane-penetrating cAMP analogs, e.g., db-cAMP and an inhibitor that inhibits their degradation (e.g., IBMX). The expected dependence of the sperm function of sAC was confirmed only recently by a genetic deletion model, a so-called knock-out mouse (G. Esposito et al. 2004 PNAS 101(9):2993ff). Male mice in which the gene for sAC is lacking show a normal spermatogenesis but are infertile. The sperm have motility defects and are not able to fertilize an egg. The animals showed no other defects or abnormal findings, which corresponds to other hypothesized functions of the sAC (J. H. Zippin et al 2003 FASEB 17:82ff)).

The sAC has a unique sequence and only a slight homology to other somatic adenylate cyclases. It is the sole adenylate cyclase in mammal sperm, and the activity is essential to the mobility of the sperm and the capacitation. Specific inhibitors of sAC accordingly represent an important possibility of regulating male fertility.

Pharmaceutical agents that contain at least one of the compounds according to claims 1-7 are therefore subjects of this invention.

The use of the compounds according to claims 1-7 is also a subject of this invention.

To use the compounds according to the invention as pharmaceutical agents, the latter are brought into the form of a pharmaceutical preparation that in addition to the active ingredient for enteral or parenteral administration contains suitable pharmaceutical, organic or inorganic inert carrier materials, such as, for example, water, gelatin, gum arabic, lactose, starch, magnesium stearate, talc, vegetable oils, polylalkylene glycols, etc. The pharmaceutical preparations can be present in solid form, for example as tablets, coated tablets, suppositories, or capsules, or in liquid form, for example as solutions, suspensions, or emulsions. Moreover, they optionally contain adjuvants, such as preservatives, stabilizers, wetting agents or emulsifiers, salts for altering the osmotic pressure, or buffers. These pharmaceutical preparations are also subjects of this invention.

For parenteral administration, in particular injection solutions or suspensions, in particular aqueous solutions of active compounds in polyhydroxyethoxylated castor oil, are suitable.

As carrier systems, surface-active adjuvants, such as salts of bile acids or animal or plant phospholipids, but also mixtures thereof as well as liposomes or their components can also be used.

For oral administration, in particular tablets, coated tablets or capsules with talc and/or hydrocarbon vehicles or binders, such as, for example, lactose, corn or potato starch, are suitable. The administration can also be carried out in liquid form, such as, for example, as a juice, to which optionally a sweetener is added.

For the vaginal application, e.g., suppositories are suitable and common.

The enteral, parenteral and oral administrations are also subjects of this invention.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose that is to be administered once or subdivided into 2 or more daily doses.

The compounds of general formula I according to the invention are, i.a., excellent inhibitors of the soluble adenylate cyclase. Inhibitors of the soluble adenylate cyclase lead to a reduction of the cAMP signal. The cAMP level is decisive for the monitoring of the processes that play an important role in cell proliferation, cell differentiation and apoptosis. Diseases, such as, e.g., cancer, in which the reduction of the cAMP level is decisive, can be modulated by inhibitors of soluble adenylate cyclase. This modulation can have prophylactic and therapeutic effects for the patients that suffer from such a disease. Diseases that, like cancer, are accompanied by an elevated cell proliferation are currently treated by, e.g., radiation therapy and chemotherapy. These processes are non-specific and have a high potential for side effects. The preparation of new substances that directly attack specific target sites is therefore advantageous. Substances that modulate the cAMP production by the inhibition of soluble adenylate cyclases are subjects of this invention. Thus, for example, the anomal cell proliferation can be reduced or inhibited by regulation or inhibition of the cAMP production. By the use of the substances according to the invention, the soluble adenylate cyclase can be inhibited; this has the result of a reduction of the cell proliferation. Subjects of this invention are pharmaceutical agents for treating diseases that contain at least one compound according to general formula I, as well as pharmaceutical agents with suitable formulation substances and vehicles. The diseases are thus characterized in that they are caused by disorders of the metabolism of the second messenger cAMP.

A reduction of the cAMP concentration by inhibition of the soluble adenylate cyclase can make available agents for modulation of the sperm capacitation. A subject of this invention is the use of the substances according to the invention for reduction and/or inhibition of male gamete fertility mediated by the reduction or inhibition of soluble adenylate cyclase activity and the thus resulting sperm capacitation.

The fertilization of the ovum can be prevented by the administration of an effective amount of a substance that results in the inhibition of the cAMP production. The use of the compound of general formula I for the production of a pharmaceutical agent for non-hormonal contraception is also a subject of this invention.

If the production of the starting compounds is not described, the latter are known or can be produced analogously to known compounds or to processes that are described here. It is also possible to implement all reactions that are described here in parallel reactors or by means of combinatory operating procedures.

The isomer mixtures can be separated into enantiomers or E/Z isomers according to commonly used methods, such as, for example, crystallization, chromatography or salt formation.

The production of salts is carried out in the usual way by a solution of the compound of formula I being mixed with the equivalent amount of or an excess of a base or acid, which optionally is in solution, and the precipitate being separated or the solution being worked up in the usual way.

Production of the Compounds According to the Invention

The examples below explain the production of the compounds of general formula (I) according to the invention, without limiting the scope of the claimed compounds to these examples.

The compounds of general formula (I) according to the invention can be produced as described below.

EXAMPLE 1

(E)-3-[5-(4-tert-Butyl-phenylsulfonylamino)-3-phenyl-1H-indol-2-yl]-N-(tetrahydro-pyran-4-yl)-acrylic acid amide

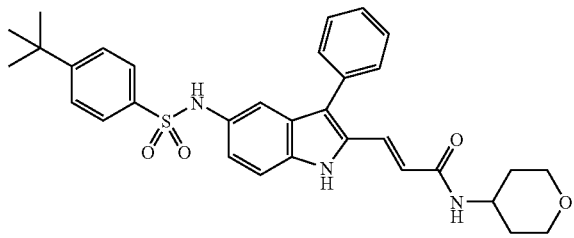

43.7 mg of N-[(dimethylamino)-1H-1,2,3-triazolo[4,5-b]pyridin-1-ylmethylene]-N-methylmethanaminiumhexafluorophosphate-N-oxide (HATU) and 10.7 mg of 4-aminotetrahydropyran are added to a solution of 50 mg of the acid, produced in Example 1h), in 0.84 ml of dimethylformamide. At 0° C., 19.5 μl of ethyldiisopropylamine is then added in drops and stirred for 20 hours at room temperature. Then, 15 ml of water is added, stirred for 30 minutes and suctioned off. The thus obtained residue is purified by chromatography on silica gel with hexane/0-70% ethyl acetate. In this way, 44 mg of the title compound is obtained.

NMR (300 MHz, DMSO-d6): δ=1.20 (s, 9H), 1.42 (2H), 1.68 (2H), 3.32 (2H), 3.79 (3H), 6.48 (1H), 6.99 (1H), 7.10 (1H), 7.20 (2H), 7.28 (1H), 7.36 (1H), 7.37 (1H), 7.42-7.53 (4H), 7.57 (2H), 8.13 (1H), 9.79 (1H), 11.63 (1H).

The starting material for the above-mentioned title compound is produced as follows:

1a) 5-Amino-1H-indole-2-carboxylic acid ethyl ester

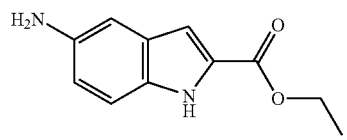

5 g of 5-nitro-1H-indole-2-carboxylic acid ethyl ester is introduced into 170 ml of methanol and 0.5 ml of water, mixed with 6.73 g of ammonium formate and with 50 mg of palladium on carbon (10%) and refluxed for 1 hour at 90° C. Then, it is suctioned off on Celite and rewashed with warm methanol. After the solvent is removed, the residue is mixed with 100 ml of water, stirred for 10 minutes, and the precipitated solid is suctioned off on a G4 frit. The thus obtained solid is dried in a vacuum. In this way, 4.12 g of the title compound is obtained.

NMR (300 MHz, DMSO-d6): δ=1.28 (3H), 4.25 (2H), 4.63 (2H), 6.62-6.68 (2H), 6.79 (1H), 7.12 (1H), 11.35 (1H).

1b) 5-(4-tert-Butyl-phenylsulfonylamino)-1H-indole-2-carboxylic acid ethyl ester

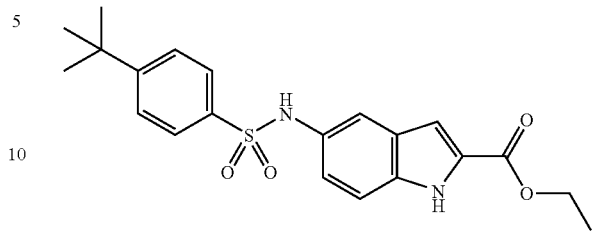

5.18 ml of ethyldiisopropylamine and 4.69 g of 4-tert-butyl-phenylsulfonyl chloride are added to a solution of 4.12 g of the amine, produced in Example 1a), in 195 ml of DMF at 0° C., and it is stirred for two hours at room temperature. The solvent is removed under reduced pressure, and the residue is purified by chromatography on silica gel with hexane/0-80% ethyl acetate. In this way, 7.56 g of the title compound is obtained.

NMR (300 MHz, DMSO-d6): δ=1.20 (9H), 1.27 (3H), 4.27 (2H), 6.97-7.03 (2H), 7.25 (1H), 7.31 (1H), 7.48 (2H), 7.59 (2H), 9.93 (1H), 11.80 (1H).

1c) 3-Bromo-5-(4-tert-butyl-phenylsulfonylamino)-1H-indole-2-carboxylic acid ethyl ester

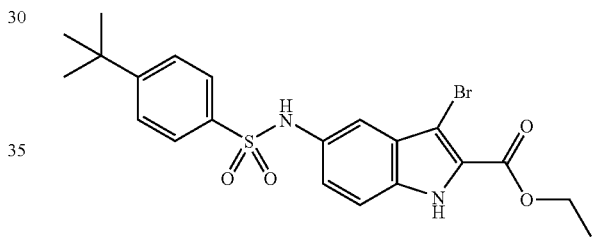

3.36 g of N-bromosuccinimide is added to a solution of 7.56 g of the sulfonamide, produced in Example 1b), in 217 ml of tetrahydrofuran, and it is stirred for 40 minutes at room temperature. It is diluted with 300 ml of ethyl acetate, washed once with 50 ml of water, twice with 50 ml each of saturated sodium chloride solution, and the organic phase is dried on sodium sulfate. After filtration and concentration by evaporation in a vacuum, the thus obtained residue is recrystallized from hexane/ethyl acetate. In this way, 8.11 g of the title compound is obtained.

NMR (300 MHz, DMSO-d6): δ=1.20 (9H), 1.30 (3H), 4.31 (2H), 7.08-7.15 (2H), 7.33 (1H), 7.50 (2H), 7.60 (2H), 10.08 (1H), 12.16 (1H).

1d) 5-(4-tert-Butyl-phenylsulfonylamino)-3-phenyl-1H-indole-2-carboxylic acid ethyl ester

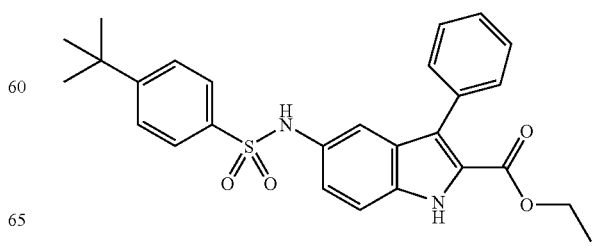

4.86 g of phenylboronic acid and 70 ml of a 1 M aqueous sodium carbonate solution as well as 3.29 g of lithium chloride are added to a solution of 13.3 g of the above-produced bromide in a mixture that consists of 531 ml of ethanol and 531 ml of toluene. After 2.58 g of tetrakis(triphenylphosphine)-palladium is added, the reaction mixture is refluxed for 20 hours. After cooling to room temperature, it is suctioned off on Celite and rewashed with ethyl acetate. The thus obtained organic phase is washed with 500 ml of saturated sodium bicarbonate and saturated sodium chloride solution and dried on sodium sulfate. After concentration by evaporation in a vacuum, the thus obtained residue is purified by chromatography on silica gel with hexane/0-70% ethyl acetate. In this way, 10.8 g of the title compound is obtained.

NMR (300 MHz, DMSO-d6): δ=1.12 (3H), 1.21 (9H), 4.15 (2H), 7.03 (1H), 7.08 (1H), 7.21-7.41 (6H), 7.49 (2H), 7.52 (2H), 9.79 (1H), 11.84 (1H).

1e) 5-(4-tert-Butyl-phenylsulfonylamino)-3-phenyl-1H-indole-2-methanol

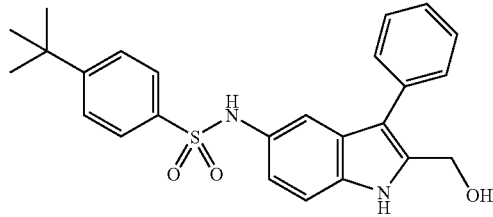

65 ml of a 1.2 molar solution of diisobutylaluminum hydride in toluene is slowly added in drops to a solution, cooled to −70° C., of 10.3 g of the ester, produced in Example 1d), in 93 ml of toluene. After the addition, it is heated to 0° C. and stirred at this temperature for 2 hours. Then, 4.3 ml of isopropanol is carefully added, and after 10 minutes, 29 ml of water is added in drops and stirred for 2 hours at room temperature. The white precipitate is filtered off, washed with 40 ml of ethyl acetate, and the thus obtained organic phase is concentrated by evaporation in a vacuum. The residue is purified by chromatography on silica gel with hexane/0-70% ethyl acetate. In this way, 4.2 g of the title compound is obtained.

NMR (300 MHz, DMSO-d6): δ=1.25 (9H), 4.60 (2H), 5.34 (1H), 6.91 (1H), 7.18 (1H), 7.23-7.34 (4H), 7.39-7.49 (2H), 7.54 (2H), 7.59 (2H), 9.72 (1H), 11.31 (1H).

1f) 5-(4-tert-Butyl-phenylsulfonylamino)-3-phenyl-1H-indole-2-carbaldehyde

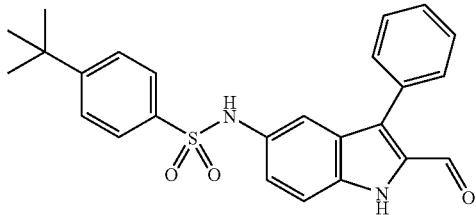

While being stirred at room temperature, 800 mg of manganese dioxide is added in portions to a solution of 500 mg of the alcohol, produced in Example 1e), in 7.5 ml of methylene chloride, and it is stirred for another 18 hours at this temperature. Then, it is suctioned off on Celite and rewashed well with ethyl acetate. After the organic phase is concentrated by evaporation in a vacuum, 330 mg of the title compound, which is incorporated without further purification into the next stage, is obtained.

NMR (300 MHz, DMSO-d6): δ=1.20 (9H), 7.15 (1H), 7.26 (1H), 7.33-7.60 (10H), 9.71 (1H), 9.93 (1H), 12.05 (1H).

1g) (E)-3-[5-(4-tert-Butyl-phenylsulfonylamino)-3-phenyl-1H-indol-2-yl]-acrylic acid ethyl ester

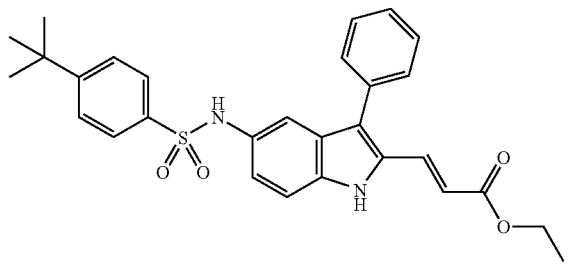

A solution of 511 mg of triethylphosphonoacetate in 1.5 ml of dimethoxyethane is added in drops at 0° C. under nitrogen to a suspension of 106 mg of NaH in 1.5 ml of dimethoxyethane, and stirring is continued for 1 more hour at room temperature. Then, a solution of the aldehyde, produced in Example 1f), in 1.5 ml of dimethoxyethane is added in drops and stirred first for 1 hour at room temperature, then for 1 hour at 50° C. After the cooling, 10 ml of saturated ammonium chloride solution is added, and after phase separation, the aqueous phase is extracted three times with 30 ml each of diethyl ether. The combined organic phases are washed once with 20 ml of water and once with 20 ml of saturated sodium chloride solution. After the drying on sodium sulfate and filtration, it is concentrated by evaporation in a vacuum. The thus obtained residue is purified by chromatography on silica gel with hexane/0-70% ethyl acetate. In this way, 280 mg of the title compound is obtained.

NMR (300 MHz, DMSO-d6): δ=1.18 (3H), 1.20 (9H), 4.11 (2H), 6.57 (1H), 7.04 (1H), 7.11 (1H), 7.18-7.32 (3H), 7.35-7.63 (8H), 9.83 (1H), 11.74 (1H).

1h) (E)-3-[5-(4-tert-Butyl-phenylsulfonylamino)-3-phenyl-1H-indol-2-yl]-acrylic acid

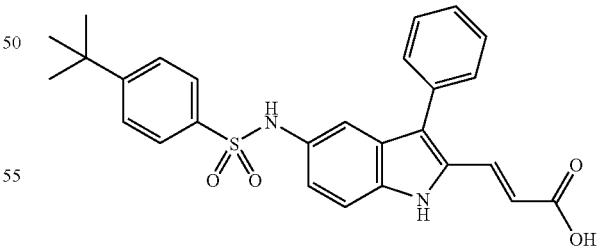

383 mg of sodium hydroxide is added to a mixture of 260 mg of the ester, produced in Example 1g), in 6.1 ml of ethanol and 3.1 ml of ethanol, and it is stirred for 17 hours at room temperature. Then, it is diluted with 30 ml of water and acidified with 5% sulfuric acid. The deposited precipitate is filtered off and dried. In this way, 225 mg of the title compound, which is further reacted without additional purification, is obtained.

NMR (300 MHz, DMSO-d6): δ=1.20 (9H), 6.48 (1H), 7.03 (1H), 7.11 (1H), 7.18-7.31 (3H), 7.34-7.61 (8H), 9.82 (1H), 11.72 (1H), 12.20 (1H).

EXAMPLE 2

(E)-3-[5-(4-tert-Butyl-phenylsulfonylamino)-3-phenyl-1H-indol-2-yl]-N-(2-morpholin-4-yl-ethyl)-acrylic acid amide

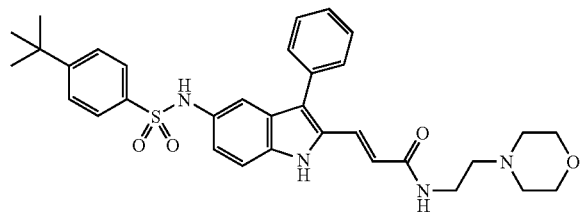

Analogously to Example 1, 43.0 mg of the title compound is obtained from 50 mg of the acid from Example 1h) and 13.8 μl of 2-(morpholin-4-yl)-ethylamine.

NMR (300 MHz, DMSO-d6): δ=1.20 (9H), 2.30-2.38 (6H), 3.24 (2H), 3.52 (4H), 6.51 (1H), 7.00 (1H), 7.10 (1H), 7.20 (2H), 7.27 (1H), 7.33 (1H), 7.36 (1H), 7.43-7.53 (4H), 7.56 (2H), 8.03 (1H), 9.79 (1H), 11.85 (1H).

EXAMPLE 3

(±)-(E)-3-[5-(4-tert-Butyl-phenylsulfonylamino)-3-phenyl-1H-indol-2-yl]-N-(2-hydroxy-1-methyl-ethyl)-acrylic acid amide

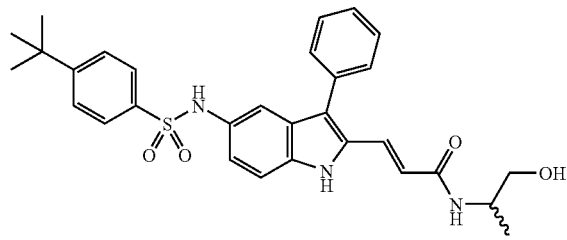

Analogously to Example 1, 44 mg of the title compound is obtained from 50 mg of the acid from Example 1h) and 8.39 μl of 2-amino-1-propanol.

NMR (300 MHz, DMSO-d6): δ=1.02 (3H), 1.21 (9H), 3.19-3.39 (2H), 3.83 (1H), 4.67 (1H), 6.50 (1H), 7.00 (1H), 7.10 (1H), 7.20 (2H), 7.28 (1H), 7.34 (1H), 7.35 (1H), 7.43-7.53 (4H), 7.56 (2H), 7.92 (1H), 9.79 (1H), 11.62 (1H).

EXAMPLE 4

(±)-(E)-3-[5-(4-tert-Butyl-phenylsulfonylamino)-3-phenyl-1H-indol-2-yl]-N-(2-hydroxy-propyl)-acrylic acid amide

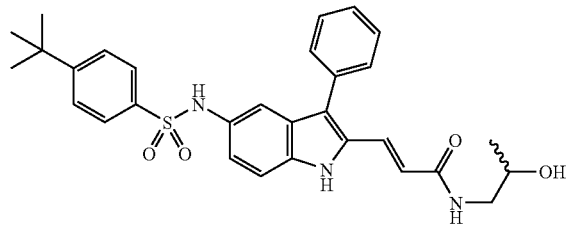

Analogously to Example 1, 47 mg of the title compound is obtained from 50 mg of the acid of Example 1h) and 8.24 μl of 1-amino-2-propanol.

NMR (300 MHz, DMSO-d6): δ=0.99 (3H), 1.21 (9H), 3.06 (2H), 3.66 (1H), 4.68 (1H), 6.54 (1H), 7.00 (1H), 7.10 (1H), 7.20 (2H), 7.28 (1H), 7.34 (1H), 7.36 (1H), 7.43-7.53 (4H), 7.56 (2H), 8.11 (1H), 9.79 (1H), 11.63 (1H).

EXAMPLE 5

3-[5-(4-tert-Butyl-phenylsulfonylamino)-3-phenyl-1H-indol-2-yl]-N-(2-morpholin-4-yl-ethyl)-propionic acid amide

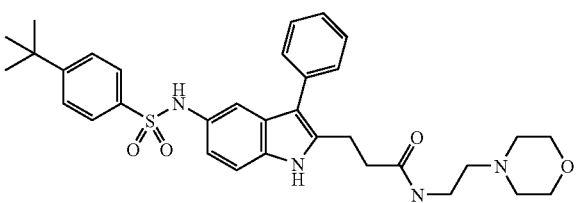

2.5 mg of palladium on carbon (10%) is added to a solution of 25 mg of the title compound, produced in Example 2), in 1.0 ml of ethyl acetate, and it is stirred for 21 hours at room temperature in a hydrogen atmosphere. Then, it is suctioned off on Celite, rewashed well with ethyl acetate, and the organic phase is concentrated by evaporation in a vacuum. The thus obtained residue is purified by preparative thin-layer chromatography on silica gel plates with ethyl acetate/acetone in a 1:1 ratio. In this way, 6.7 mg of the title compound is obtained.

NMR (300 MHz, DMSO-d6): δ=1.21 (9H), 2.18-2.38 (6H), 2.92 (2H), 3.11 (2H), 3.25-3.35 (2H), 3.47 (4H), 6.83 (1H), 7.05 (1H), 7.17-7.27 (4H), 7.39 (2H), 7.50 (2H), 7.56 (2H), 7.73 (1H), 9.66 (1H), 11.05 (1H).

BIOLOGICAL EXAMPLES

Example 1 sAC-Assay

In a suitable buffer system, the soluble, sperm-specific adenylate cyclase catalyzes the reaction of adenosine triphosphate (ATP) to cyclic adenosine monophosphate (cAMP) and pyrophosphate. Free cAMP that is generated in this way is then used in a competitive detection process, in which the binding of a europium kryptate (Eu[K])-labeled anti-cAMP antibody (anti cAMP-Eu[K]-AK) to a cAMP-molecule-labeled, modified allophycocyanine-1 molecule (cAMP-XL665) is prevented. In the absence of exogenic cAMP, after excitation at 335 nm, it results in a fluorescence resonance energy transfer (FRET) between the anti cAMP-Eu[K]-AK (FRET-donor) and the cAMP-XL665 molecule (FRET-acceptor). This process is quantified at different times (time-resolved) based on the emission of FRET-acceptor XL665 (665 nm and 620 nm). A signal drop (measured as a wave ratio; calculation formula: [(E665 nm/E620 nm)×10000]) can be attributed to the presence of cAMP and thus to the activity of sAC.

First, 1.5 µl of the test substance (in 30% DMSO), only 30% DMSO in the solvent controls, is introduced per recess in a 384-hole test plate (polystyrene; 384, NV). Then, 10 µl of a dilute sAC enzyme solution is recovered (enzyme stock solution in 300 mmol of NaCl, 10% glycerol; pH 7.6; intermediate and final enzyme dilution a) 1:10 and b) 1:2000 in each case in: 1.0 mmol of $MnCl_2$; 0.2% BSA; 50 mmol of tris, pH 7.5 in $H_2O$). The enzyme reaction is started by adding 5 µl of the ATP-substrate solution (200 µmol of ATP in $H_2O$) and is completed after incubation (25 minutes at room temperature) by the addition of 5 µl of stop solution (200 µmol of EDTA in PBS). Finally, the entire reaction is adjusted to a total volume of 91.5 µl by adding 70 µl of PBS.

Then, 8 µl of detection solution 1 is introduced into a recess of the 384-hole measuring plate (measuring plate: polystyrene; 384, SV—black; detection solution 1: 50 µl of cAMP-XL665; 950 µl of reconstitution buffer; 2200 µl of PBS; cAMP-XL665: production by the addition of 5 ml of $H_2O$ to the freeze-dried product as specified by Cis Bio Kit: #62AMPPEC instructions; storage: aliquoted at −80° C.). Then, 3 µl from the 91.5 µl is added to the corresponding recess of the test plate. Finally, the addition of 8 µl of detection solution 2 (detection solution 2: 50 µl of anti cAMP-Eu [K]-AK; 950 µl of reconstitution buffer; 2200 µl of PBS; anti cAMP-Eu[K]-AK: production as specified by Cis Bio Kit: #62AMPPEC instructions; storage: aliquoted at −80° C.) is carried out.

After an additional incubation of 90 minutes at room temperature, the HTRF result is measured either on the Packard Discovery or with the RubiStar HTRF measuring device (Delay: 50 µs; Integration time: 400 µs).

Example 2

Isolation of Human Sperm from Ejaculates and Capacitation 2.1. Isolation of Sperm:

Human sperm are purified from the ejaculate by a two-layer gradient system based on colloidal silica particles (trade name: Percoll or ISolate).

Per ejaculate, 2.5 ml each of a preheated lower layer ("90% ISolate lower layer," Irvine Company) is introduced into a 15 ml centrifuging tube (conical, plastic) and carefully covered with 2.5 ml of a preheated upper layer ("50% ISolate upper layer," Irvine Company) and held back in a water bath at 37° C. for <1 hour. The gradient is carefully coated with a maximum of 3 ml of normal (relative to the number of sperm, motility and liquefaction) ejaculate. The sedimentation of sperm is carried out at 1000×g for 25 minutes at room temperature. By means of a glass capillary, both layers are suctioned off to a point just above the sperm pellets. To wash out the ISolate gradients, the sperm pellets that are resuspended in about 200 µl each are moved into a 15 ml plastic tube with 12 ml of mHTF medium (4 mmol of $NaHCO_3$; 0.01% BSA; 37° C.), and the sperm are sedimented at 1000×g for 20 minutes. The medium is suctioned off to a point just above the pellet and adjusted to 1000 µl with mHTF medium (4 mmol of $NaHCO_3$; 0.01% BSA; 37° C.). The number of sperm is determined in a Neubauer counting chamber, and adjusted for the following capacitation optionally with mHTF medium (4 mmol of $NaHCO_3$; 0.01% BSA; 37° C.) to 4×106 sperm/ 150 µl.

2.2. Capacitation

If the effect of test substances on the acrosomal reaction is to be tested, the sperm must be pre-incubated with the test substances. This pre-incubation (15 minutes in the incubator at 37° C.) is necessary to make possible the penetration of test substances in the sperm before the beginning of capacitation, i.e., to achieve a pre-saturation of the binding sites in the sperm, in particular in substances that do not pass through the membrane well. In addition, it is necessary since the increase of the BSA concentration in the capacitation by the high lipid bond of the BSA could result in the reduction of the effective test substance concentration in the preparation.

The test substances are dissolved in DMSO and diluted with mHTF medium (4 mmol of $NaHCO_3$; 0.01% BSA; 37° C.), such that in the final capacitation preparation of 400 µl, the DMSO concentration is 0.5%. 150 µl each of the tempered test substance solution above is pipetted in each case into 150 µl of sperm suspension and pre-incubated for 15 minutes at 37° C. The capacitation of sperm is started by adding 100 µl of mHTF-medium (88 mmol of $NaHCO_3$; 4% BSA; 37° C.). In the final 400 µl of capacitation preparation, the sperm concentration is 10×106/ml, the bicarbonate concentration is 4 mmol, and the BSA concentration is 1%. The capacitation is carried out at 37° C. for 3 hours in an incubator.

To complete the capacitation, the preparations (400 µl each) are each transferred completely into a 15 ml sample tube with 1.5 ml of mHTF (4 mmol of $NaHCO_3$; 37° C.), centrifuged for 5 minutes at 1000×g, and the supernatant is removed. With this step, both the high amount of protein and the test substances are removed.

Example 3

Flow-Cytometric Determination of the Acrosomal Reaction 3.1. Introduction of the Acrosomal Reaction by Ionophore Treatment and Simultaneous CD46-FITC Staining The acrosomal reaction (AR) of the sperm is triggered by the binding of the sperm to the Zona pellucida (ZP). In this case, enzymes are released from the acrosome that make it possible for the sperm to penetrate the ovocyte through the ZP. In the case of AR, in sperm, it results in a partial merging of the plasma membrane with the outside acrosomal membrane (OAM). The head of the sperm cell is limited only by the inside acrosomal membrane (IAM) at the end. The CD46-antigen can be detected only on the IAM.

The acrosomal reaction can be induced in vitro with a suitable concentration of the calcium-ionophore A23187 on capacitated sperm, but not on uncapacitated sperm or on sperm that are inhibited in capacitation by test substances. With the aid of FITC-labeled anti-CD46 antibodies (Pharmingen Company) against the IAM, the acrosome-reacted sperm can be distinguished in the flow cytometer from the acrosome-intact sperm, in which the IAM is not exposed. By the simultaneous staining of the sperm with the DNA dye ethidium homodimer (EhD), which stains only the DNA membrane-defective, thus dead cells, the dead sperm can be distinguished from the living sperm.

Since the ionophore dilutions seem to be very unstable in triggering the AR and must be mixed for the simultaneous staining with the CD46-FITC solution, the solutions cannot be prepared before the beginning of the test but rather must be produced during the working-up of the capacitation preparations.

The sperm pellets are resuspended in the residual supernatant and are diluted in a water bath (37° C.) with 450 µl of mHTF (4 mmol of $NaHCO_3$; 0.01% BSA; 37° C.). 100 µl Aliquots of the sperm suspensions are pipetted into prepared FACS-flow tube samples (in a water bath). 150 µl of a solution with ionophore and FITC-labeled anti-CD46 antibodies are pipetted into the sperm. The final concentration is 800 nmol of ionophore and a 1:125 dilution of the anti-CD46 antibody in mHTF (4 mmol of $NaHCO_3$; 0.01% BSA; 37° C.). The sperm are incubated therein, protected from light, for 30 minutes in a water bath at 37° C.

The incubation is stopped by adding 3.5 ml of PBS [0.1% BSA]/preparation, followed by centrifuging for 5 minutes at 700×g (room temperature) and subsequent suctioning-off of the supernatants. After the centrifuging, the samples are kept warm on the hot plate until the measurement is done.

3.2. EhD Staining (for Differentiation of Dead/Living Acrosomally-Reacted Sperm)

After suctioning-off, the sperm pellets are mixed with 500 µl each of freshly prepared EhD solution (150 nmol of EhD in PBS [w/o BSA]; 37° C.). The samples can then be measured in a flow cytometer (BD Facs Calibur). The measurement is done at a laser excitation wavelength of 488 nm; 10,000 sperm per measurement are detected. Acrosome-reacted sperm are measured with CD46-FITC in an FL-1 filter at 530 nm. Dead sperm are measured by means of EhD-DNA-staining in an FL-2 filter at 634 nm. The measuring channels are first compensated appropriately with respect to one another.

3.3 Evaluation:

The sperm are selected as a very uniform cell population in an FSC-H (forward scatter) from SSC-H (sideward scatter) Dotblot. Since a two-color fluorescence staining is used, the evaluation is carried out with the aid of a quadrant analysis in an FL-1 (EhD, X-axis) vs. FL-2 (FITC-CD46, Y-axis) Dotblot with the selected sperm population from the FSC vs. SSC Dotblot:

| | Quadrant in FL-1 vs. FL-2 Dotblot | Staining | Analysis |
|---|---|---|---|
| Q1 = UL | Upper left | Only EhD | Dead, non-acrosomally-reacted sperm |
| Q2 = UR | Upper right | EhD and FITC-CD46 | Dead, acrosomally-reacted sperm |
| Q3 = LL | Lower left | Unstained | Living, non-acrosomally-reacted sperm |
| Q4 = LR | Lower right | Only FITC-CD46 | Living, acrosomally-reacted sperm |

To calculate the % of induced, acrosomally-reacted sperm (="IAR[%]"), only the living sperm from Q3 and Q4 are used, and their total number is set at equal to 100%. IAR is then calculated as follows:

$$IAR[\%] = \frac{LR \times 100}{LL + LR}$$

A portion of the sperm already reacts spontaneously acrosomally without the addition of ionophore (="SAR[%]"). Therefore, a control measurement of identically-treated sperm without the addition of an ionophore is always also taken. The SAR is calculated analogously to the IAR. The acrosomal reaction (="ARIC[%]") that is actually triggered by the ionophore is calculated as the difference: ARIC=IAR−SAR.

For the following analysis of the effect of our inhibitors on the sAC-mediated capacitation (measured as the ability of the sperm to undergo ionophore-induced acrosomal reaction), the percentage of acrosomally-reacted sperm in the positive capacitation control (=incubation with mHTF medium with 25 mmol of NaHCO3; 1% BSA without test substances) is set at =100%. The ability of the sperm mixed with the test substances to undergo acrosomal reaction is indicated relative to this maximum acrosomal reaction.

Materials Used mHTF=modif. human tubular fluid (Irvine Scientific Company), Dulbecco's phosphate-buffered saline (Gibco Company) (with $Ca^{2+}$, $Mg^{2+}$, 1 g/l of D-glucose, 36 mg/l of Na-pyruvate, w/o phenol red, w/o $NaHCO_3$); bovine serum albumin, Fraction V (Fluka Company); dimethyl sulfoxide (DMSO), anhydrous (Merck Company); Sodium Bicarbonate 7.5% solution (893 mmol) (Irvine Scientific Company); isolate gradient (Irvine Scientific Company); Ionophore-A23187 free acid, (Calbiochem Company); ethidium homodimer (EhD) (Molecular Probe Company), Mouse Anti Human CD46:FITC (Pharmingen Company).

Bibliographical References

J. W. Carver-Ward, Human Reproduction Vol. 11, No. 9, pp: 1923 ff, 1996 High Fertilization Prediction by Flow-Cytometric Analysis of the CD46 Antigen on the Inner Acrosomal Membrane of Spermatozoa O. J. D'Cruz, G. G. Haas, Fertility and Sterility Vol. 65, No. 4, pp: 843 ff, 1996 Fluorescence-Labeled Fucolectins are Superior Markers for Flow-Cytometric Quantitation of the Sperm Acrosome Reaction E. Nieschlag, H. M. Behre, Andrologie [Andrology], Springer Verlag 1996

EXAMPLES

| # | R⁴ | Y | IC50 (μM) |
|---|---|---|---|
| 2 | [structure: 4-tert-butylphenylsulfonamido-indole with phenyl, carboxamide-ethyl-morpholine] | —CH=CH— | 3.5 |
| 4 | [structure: 4-tert-butylphenylsulfonamido-indole with phenyl, carboxamide-CH₂-CH(OH)] | —CH₂—CHCH₃—OH —CH=CH— | 4.4 |
| 4-OH-Estradiol | [structure: 4-OH-Estradiol, Chiral] | | 13 |
| 2-OH-Estradiol | [structure: 2-OH-Estradiol, Chiral] | | 11 |

It can be seen from the table that the compounds according to the invention relative to the inhibition of the soluble adenylate cyclase, expressed by the $IC_{50}$ value, sometimes have a higher activity than the already known catechol estrogens (OH-estradiols). The catechol estrogens are toxic, therefore the compounds according to the invention are far superior to the known compounds. The compounds according to the invention are also more powerful than the compounds presented by Zippin.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 10 2005 014 324.8, filed Mar. 23, 2006, and U.S. Provisional Application Ser. No. 60/788,075 filed Apr. 3, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I),

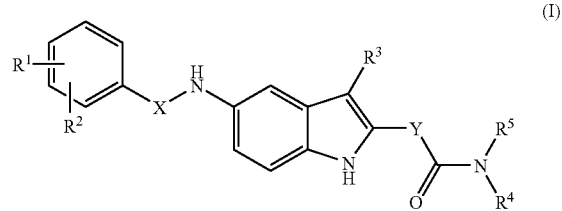

wherein

R$^1$ is hydrogen, halogen, CF$_3$, C$_3$-C$_6$-cycloalkyl, which optionally is polysaturated and optionally is polysubstituted, C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl, or C$_1$-C$_6$-aryl-C$_1$-C$_6$-alkyl, wherein C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl or C$_1$-C$_6$-aryl-C$_1$-C$_6$-alkyl groups are optionally interrupted in one or more places, in the same way or differently, by oxygen, sulfur, nitrogen, sulfonyl-C$_1$-C$_6$-alkyl, sulfonamide, or cyano, R$^2$ is halogen, CF$_3$, C$_3$-C$_6$-cycloalkyl which optionally is polysaturated and optionally is polysubstituted, C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-acyl, C$_1$-C$_6$-acyl-C$_1$C$_6$-acyl, C$_1$-C$_6$-alkyl-C$_1$-C$_6$-aryl, or C$_1$-C$_6$-aryl-C$_1$-C$_6$-alkyl, wherein C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl, or C$_1$-C$_6$-aryl-C$_1$-C$_6$-alkyl groups are optionally interrupted in one or more places, in the same way or differently, by oxygen, sulfur, nitrogen, sulfonyl-C$_1$-C$_6$-alkyl, sulfonamide, or cyano, R$^3$ is C$_6$-C$_{12}$-aryl, which is optionally substituted in one or more places, in the same way or differently, by halogen, C$_1$-C$_6$-alkyl, C$_1$-C$_6$-alkoxy, hydroxy, cyano, CO$_2$—(C$_1$-C$_6$-alkyl), N—(C$_1$-C$_6$-alkyl)$_2$, CO—NR$^4$R$^5$, CF$_3$ or C$_1$-C$_6$-acyl;

C$_5$-C$_{12}$-heteroaryl, which optionally is substituted in one or more places, in the same way or differently, by halogen, C$_1$-C$_6$-alkyl, C$_1$-C$_6$-acyl, C$_1$-C$_6$-alkoxy, hydroxy, cyano, CO$_2$—(C$_1$-C$_6$-alkyl), N—(C$_1$-C$_6$-alkyl)$_2$, CO—NR$^4$R$^5$ or CF$_3$; or C$_3$-C$_6$-cycloalkyl, which optionally is substituted in one or more places, in the Same way or differently, by halogen, CF$_3$, hydroxy, cyano, CO$_2$—(C$_1$-C$_6$-alkyl), C$_1$-C$_6$-alkyl, C$_1$-C$_6$-acyl, N—(C$_1$-C$_6$-alkyl)$_2$, CO—NR$^4$R$^5$ or C$_1$-C$_6$-alkoxy, R$^4$ is hydrogen, or C$_3$-C$_6$-cycloalkyl, which optionally is substituted in one or more places, in the same way or differently, by C$_1$-C$_6$-alkyl, C$_1$-C$_6$-acyl, C$_1$-C$_6$-alkoxy or CF$_3$;

C$_6$-C$_{12}$-aryl, which optionally is substituted in one or more places, in the same way or differently, by halogen, C$_1$-C$_6$-alkyl, C$_1$-C$_6$-acyl, C$_1$-C$_6$-alkoxy, N—C$_1$-C$_6$-alkyl-C$_1$-C$_6$-alkyl, CF$_3$ or cyano;

C$_5$-C$_{12}$-heteroaryl, which optionally is substituted in one or more places, in the same way or differently, by halogen, C$_1$-C$_6$-alkyl, C$_1$-C$_6$-acyl, C$_1$-C$_6$-alkoxy, N—C$_1$-C$_6$-alkyl-C$_1$-C$_6$-alkyl, CF$_3$ or cyano; or C$_1$-C$_6$-alkyl, which can be substituted in any way desired, R$^5$ is hydrogen, or C$_1$-C$_6$alkyl-C$_3$-C$_6$-cycloalkyl, which optionally is substituted in one or more places, in the same way or differently, by C$_1$-C$_6$-alkyl, C$_1$-C$_6$-acyl, C$_1$-C$_6$-alkoxy or CF$_3$;

C$_3$-C$_6$-cycloalkyl, which optionally is substituted in one or more places, in the same way or differently, by C$_1$-C$_6$-alkyl, C$_1$-C$_6$-acyl, C$_1$-C$_6$-alkoxy or CF$_3$;

C$_6$-C$_{12}$-aryl, which optionally is substituted in one or more places, in the same way or differently, by halogen, C$_1$-C$_6$-alkyl, C$_1$-C$_6$-acyl, C$_1$-C$_6$-alkoxy, N—C$_1$-C$_6$-alkyl-C$_1$-C$_6$-alkyl, CF$_3$ or cyano;

C$_5$-C$_{12}$-heteroaryl, which optionally is substituted in one or more places, in the same way or differently, by halogen, C$_1$-C$_6$-alkyl, C$_1$-C$_6$-acyl, C$_1$-C$_6$-alkoxy, N—C$_1$-C$_6$-alkyl-C$_1$-C$_6$-alkyl, CF$_3$ or cyano; or C$_1$-C$_6$-alkyl, which can be substituted in any way desired, R$^4$ and R$^5$ together can also form a 5- to 8-membered ring, which can contain additional heteroatoms, and X is sulfonyl, (CH$_2$)$_n$ or carbonyl, Y is —(CH$_2$)$_n$— or —CH=CH—, and n is 1-4, or or a diastereomer, or an enantiomer, or a physiologically compatible salt thereof.

2. A compound according to claim 1, wherein

R$^1$ is hydrogen, halogen, CF$_3$, C$_3$-C$_6$-cycloalkyl, C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl, C$_1$-C$_6$-aryl-C$_1$-C$_6$-alkyl or CF$_3$, wherein C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl or C$_1$-C$_6$-aryl-C$_1$-C$_6$-alkyl groups are optionally interrupted in one or more places, in the same way or differently, by oxygen, sulfur, nitrogen, or sulfonyl-C$_1$-C$_6$-alkyl, sulfonamide, or cyano, R$^2$ is halogen, CF$_3$, C$_3$-C$_6$-cycloalkyl, C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl, C$_1$-C$_6$-aryl-C$_1$-C$_6$-alkyl or CF$_3$, wherein C$_1$-C$_6$-alkyl, C$_1$-C$_6$-aryl, C$_1$-C$_6$-acyl, halo-C$_1$-C$_6$-alkyl, C$_1$-C$_6$-alkyl-C$_1$-C$_6$-alkyl, C$_1$-C$_6$-alkyl-C$_1$-C$_6$-acyl, C$_1$-C$_6$-acyl-C$_1$-C$_6$-acyl, C$_1$-C$_6$-alkyl-C$_1$-C$_6$-aryl or C$_1$-C$_6$-aryl-C$_1$-C$_6$-alkyl groups are optionally interrupted in one or more places, in the same way or differently, by oxygen, sulfur, nitrogen, or sulfonyl-C$_1$-C$_6$-alkyl, sulfonamide, or cyano, R$^3$ is C$_6$-C$_{12}$-aryl, which optionally can be substituted in one or more places, in the way or differently, by halogen, C$_1$-C$_6$-alkyl, C$_1$-C$_3$-acyl, C$_1$-C$_3$-alkoxy, cyano, hydroxy, N—(CH$_3$)$_2$, CO$_2$—(C$_1$-C$_3$-alkyl), CO—NR$^4$R$^5$ or CF$_3$;

C$_5$-C$_{12}$-heteroaryl, which optionally can be substituted in one or more places, in the same way or differently, by chlorine, fluorine, C$_1$-C$_6$-alkyl, C$_1$-C$_3$-acyl, C$_1$-C$_3$-alkoxy, cyano, hydroxy, N—(CH$_3$)$_2$, CO$_2$—(C$_1$-C$_3$-alkyl), CO—NR$^4$R$^5$ or CF$_3$; or C$_3$-C$_6$-cycloalkyl, which optionally can be substituted in one or more places, in the same way or differently, by chlorine, fluorine, CF$_3$, cyano, C$_1$-C$_3$-alkyl, C$_1$-C$_3$-acyl, hydroxy, N—(CH$_3$)$_2$, CO$_2$—(C$_1$-C$_3$-alkyl), CO—NR$^4$R$^5$ or C$_1$-C$_3$-alkoxy, $R^4$ is hydrogen, $C_3$-$C_6$-cycloalkyl, which optionally is substituted in one or more places, in the same way or differently, by $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano;

$C_5$-$C_{12}$-heteroaryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, which can be substituted in any way desired, $R^5$ is hydrogen, or $C_1$-$C_6$-alkyl-$C_3$-$C_6$-cycloalkyl, which optionally is substituted in one or more places, in the same way or differently, by $C_1$-$C_3$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, by $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano;

$C_5$-$C_{12}$-heteroaryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, which can be substituted in any way desired, $R^4$ and $R^5$ together can also form a 5- to 8-membered ring, which can contain additional heteroatoms, and X is the groups sulfonyl, $(CH_2)_n$ or carbonyl, Y is —$(CH_2)_n$— or —CH=CH—, and n is 1-2.

3. A compound according to claim 1, wherein $R^1$ is hydrogen, $R^2$ is $C_3$-$C_6$-cycloalkyl, $C_1$-$C_6$-alkyl, $CF_3$, cyano, bromine, —$OCF_3$, or —$SO_2$—$CH_3$, $R^3$ is $C_6$-$C_{12}$-aryl, which is optionally substituted in one or more places, in the same way or differently, by halogen, $C_1$-$C_6$-alkyl, $C_1$-$C_3$-acyl, $C_1$-$C_3$-alkoxy, cyano, hydroxy, N—$(CH_3)_2$, $CO_2$—$(C_1$-$C_3$-alkyl), CO—$NR^4R^5$ or $CF_3$;

$C_5$-$C_{12}$-heteroaryl, which optionally can be substituted in one or more places, in the same way or differently, by chlorine, fluorine, $C_1$-$C_6$-alkyl, $C_1$-$C_3$-acyl, $C_1$-$C_3$-alkoxy, cyano, hydroxy, N—$(CH_3)_2$, $CO_2$—$(C_1$-$C_3$-alkyl), CO—$NR^4R^5$ or with $CF_3$; or $C_3$-$C_6$-cycloalkyl, which optionally can be substituted in one or more places, in the same way or differently, by chlorine, fluorine, $CF_3$, cyano, $C_1$-$C_3$-alkyl, $C_1$-$C_3$-acyl, hydroxy, N—$(CH_3)_2$, $CO_2$—$(C_1$-$C_3$-alkyl), CO—$NR^4R^5$ or $C_1$-$C_3$-alkoxy, $R^4$ is hydrogen, $R^5$ is hydrogen, $C_1$-$C_6$-alkyl-$C_3$-$C_6$-cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, by $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano;

$C_5$-$C_{12}$-heteroaryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, which can be substituted in any way desired, X is sulfonyl, Y is —$(CH_2)_n$— or —CH=CH—, and n is 1-2.

4. A compound according to claim 1, wherein $R^1$ is hydrogen, $R^2$ is $C_3$-$C_6$-cycloalkyl, $C_1$-$C_6$-alkyl, $CF_3$, sec-butyl, cyano, bromine, or the group —$OCF_3$, or —$SO_2$—$CH_3$, and is in para-position, $R^3$ is $C_6$-$C_{12}$-aryl, which optionally is substituted in one or two places, in the same way or differently, by halogen, $C_1$-$C_3$-alkyl, acetyl, methoxy, ethoxy, cyano, hydroxy, N—$(CH_3)_2$, $CO_2$—$(C_1$-$C_3$-alkyl), CO—$NHR^5$ or $CF_3$;

$C_5$-$C_{12}$-heteroaryl, which optionally is substituted in one or two places, in the same way or differently, by chlorine, fluorine, $C_1$-$C_3$-alkyl, acetyl, methoxy, ethoxy, cyano, hydroxy, N—$(CH_3)_2$, $CO_2$—$(C_1$-$C_3$-alkyl), CO—$NHR^5$ or with $CF_3$; or $C_3$-$C_6$-cycloalkyl, $R^4$ is hydrogen, $R^5$ is hydrogen, or $C_1$-$C_6$-alkyl-$C_3$-$C_6$-cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, by $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano;

$C_5$-$C_{12}$-heteroaryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, which can be substituted in any way desired, X is sulfonyl, Y is —$(CH_2)_n$— or —CH=CH—, and n is 1-2.

5. A compound according to claim 1, wherein $R^1$ is hydrogen, $R^2$ is tert-butyl, iso-propyl, iso-butyl, sec-butyl, cyano, bromine, —O—$CF_3$, or —$SO_2$—$CH_3$, and is in para-position, R³ is

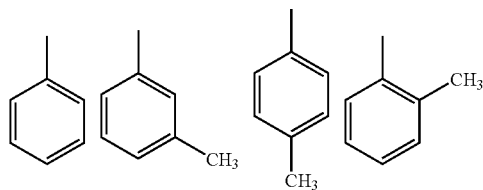

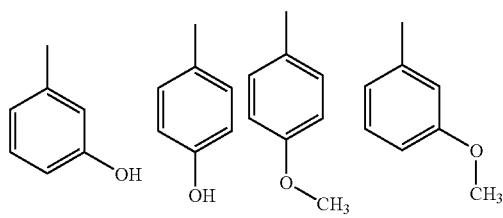

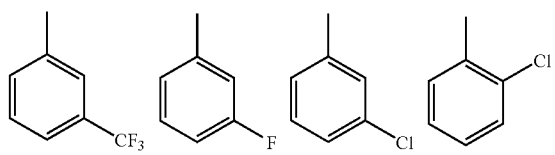

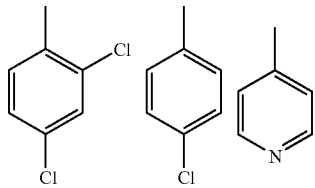 or

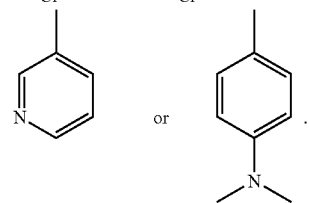.

R⁴ is hydrogen,
R⁵ is hydrogen, —(CH₂)ₙ—N—(CH₃)₂, —(CH₂)₂—CH₃,
—(CH₂)₂—NH—COCH₃, —(CH₂)—CHCH₃—OH,
—(CH₂)₂—O—CH₃, —(CH₂)₂—OH, —CHCH₃—
CH₂—OH,

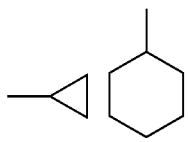

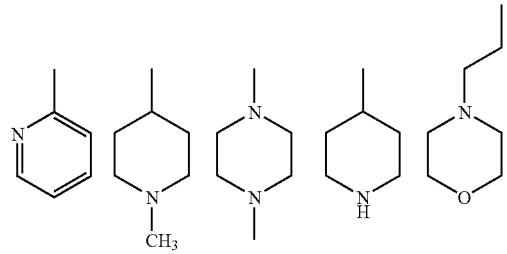

-continued

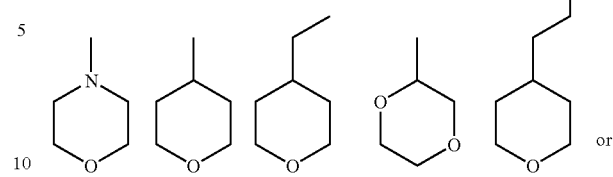

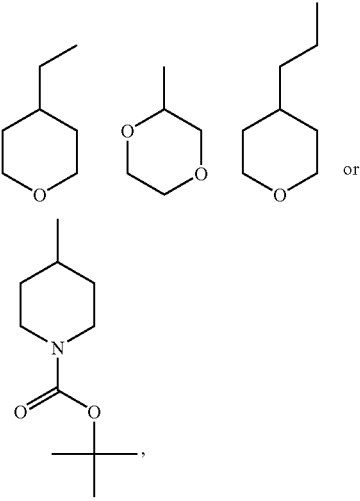

X is sulfonyl,
Y is —(CH₂)ₙ— or —CH=CH—, and
n is 1-2.

6. A compound according to claim 1, wherein
R¹ is hydrogen,
R² is tert-butyl, iso-propyl, iso-butyl, sec-butyl, cyano, bromine, —O—CF₃, or —SO₂—CH₃, and is in para-position,
R³ is

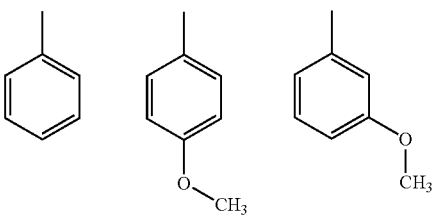

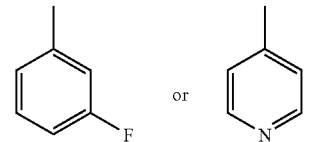.

R⁴ is hydrogen,
R⁵ is hydrogen, —(CH₂)—CHCH₃—OH, —(CH₂)₂—O—CH₃, —CHCH₃—CH₂—OH,

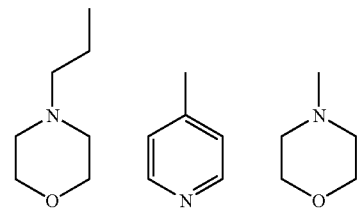

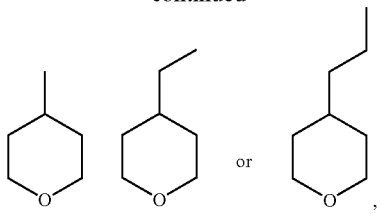

X is sulfonyl,
Y is —(CH$_2$)$_n$— or —CH═CH—, and
n is 1-2.

7. A compound according to claim 1, wherein said compound is:
1. (E)-3-[5-(4-tert-Butyl-phenylsulfonylamino)-3-phenyl-1H-indol-2-yl]-N-(tetrahydro-pyran-4-yl)-acrylic acid amide,
2. (E)-3-[5-(4-tert-Butyl-phenylsulfonylamino)-3-phenyl-1H-indol-2-yl]-N-(2-morpholin-4-yl-ethyl)-acrylic acid amide,
3. (±)-(E)-3-[5-(4-tert-Butyl-phenylsulfonylamino)-3-phenyl-1H-indol-2-yl]-N-(2-hydroxy-1-methyl-ethyl)-acrylic acid amide,
4. (±)-(E)-3-[5-(4-tert-Butyl-phenylsulfonylamino)-3-phenyl-1H-indol-2-yl]-N-(2-hydroxy-propyl)-acrylic acid amide,
5. 3-[5-(4-tert-Butyl-phenylsulfonylamino)-3-phenyl-1H-indol-2-yl]-N-(2-morpholin-4-yl-ethyl)-propionic acid amide,
6. (E)-3-[5-(4-tert-Butyl-phenylsulfonylamino)-3-(3-fluorophenyl)-1H-indol-2-yl]-N-(tetrahydro-pyran-4-yl)-acrylic acid amide,
7. (E)-3-[5-(4-tert-Butyl-phenylsulfonylamino)-3-(3-fluorophenyl)-1H-indol-2-yl]-N-(2-morpholin-4-yl-ethyl)-acrylic acid amide,
8. (E)-3-[5-(4-tert-Butyl-phenylsulfonylamino)-3-(3-methoxy-phenyl)-1H-indol-2-yl]-N-(tetrahydro-pyran-4-yl)-acrylic acid amide,
9. (E)-3-[5-(4-tert-Butyl-phenylsulfonylamino)-3-(3-methoxy-phenyl)-1H-indol-2-yl]-N-(2-morpholin-4-yl-ethyl)-acrylic acid amide,
10. (E)-3-[5-(4-tert-Butyl-phenylsulfonylamino)-3-(3-fluorophenyl)-1H-indol-2-yl]-N-(pyridin-4-yl)-acrylic acid amide, or
11. (E)-3-[5-(4-tert-Butyl-phenylsulfonylamino)-3-(3-methoxy-phenyl)-1H-indol-2-yl]-N-(pyridin-4-yl)-acrylic acid amide, or a physiologically compatible salt thereof.

8. A pharmaceutical composition comprising at least one compound according to claim 1 and a carrier.

9. A pharmaceutical composition according to claim 8, wherein said compound is contained in an amount of 0.5-1000 mg.

10. A method of achieving contraception in a patient, comprising administering to said patient a compound according to claim 1.

11. A method of inhibiting soluble adenylate cyclase in a patient, comprising administering to said patient a compound according to claim 1.

12. A pharmaceutical composition according to claim 8, wherein said composition is in a form suitable for enteral, parenteral, vaginal or oral administration.

13. A process for preparing a compound according to claim 1, said process comprising:
reacting a compound of formula (II)

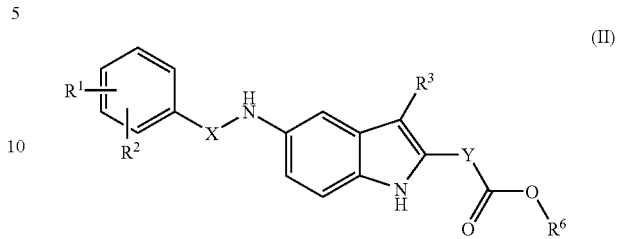

in which $R^1$, $R^2$, $R^3$, X and Y have the meanings in formula I and $R^6$ is hydrogen or $C_1$-$C_6$-alkyl, with an amine of formula III

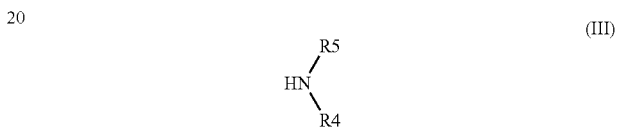

in which $R^4$ and $R^5$ have the meanings in formula I, and
optionally cleaving protective groups and/or hydrogenating double bonds, to form a compound of formula (I).

14. A method of inhibiting soluble adenylate cyclase comprising administering a compound of claim 1.

15. A compound according to claim 1, wherein acyl is formyl, acetyl, propionyl, butyroyl, iso-butyroyl, or valeroyl.

16. A compound according to claim 1, wherein cycloalkyl in each case is cyclopropyl, cyclobutyl, cyclopentyl, or cyclohexyl.

17. A compound according to claim 1, wherein heteroaryl in each case is thienyl, furanyl, pyrrolyl, oxazolyl, imidazolyl, pyrazolyl, isoxazolyl, isothiazolyl, oxadiazolyl, triazolyl, thiadiazolyl, enzofuranyl, benzothienyl, benzooxazolyl, benzimidazolyl, indazolyl, indolyl, isoindolyl, pyridazinyl, pyrimidinyl, pyrazinyl, triazinyl, quinolyl, isoquinolyl, azoinyl, indolizinyl, purinyl, quinolinyl, isoquinolinyl, cinnnnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, oxepinyl, thiophenyl, or pyridinyl.

18. A compound according to claim 1, wherein
$R^1$ is hydrogen, halogen, $CF_3$, $C_3$-$C_6$-cycloalkyl, $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, or $C_1$-$C_6$-aryl-$C_1$-$C_6$-alkyl, $R^2$ is halogen, $CF_3$, $C_3$-$C_6$-cycloalkyl, $C_1$-$C_6$-alkyl, $C_1$-$C_6$-aryl, $C_1$-$C_6$-acyl, halo-$C_1$-$C_6$-alkyl, $C_1$-$C_6$-alkyl-$C_1$-$C_6$-alkyl, $C_1$-$C_6$-alkyl-$C_1$-$C_6$-acyl, $C_1$-$C_6$-acyl-$C_1$-$C_6$-acyl, $C_1$-$C_6$-alkyl-$C_1$-$C_6$-aryl, or $C_1$-$C_6$-aryl-$C_1$-$C_6$-alkyl, $R^3$ is $C_6$-$C_{12}$-aryl, which is optionally substituted in one or more places, in the same way or differently, by halogen, $C_1$-$C_6$-alkyl, $C_1$-$C_6$-alkoxy, hydroxy, cyano, $CO_2$—($C_1$-$C_6$-alkyl), N—($C_1$-$C_6$-alkyl)$_2$, CO—$NR^4R^5$, $CF_3$ or $C_1$-$C_6$-acyl, $C_5$-$C_{12}$-heteroaryl, which optionally is substituted in one or more places, in the same way or differently, by halogen, $C_1$-$C_6$-alkyl, $C_1$-$C_6$-acyl, $C_1$-$C_6$-alkoxy, hydroxy, cyano, $CO_2$—($C_1$-$C_6$-alkyl), N—($C_1$-$C_6$-alkyl)$_2$, CO—$NR^4R^5$ or $CF_3$; or $C_3$-$C_6$-cycloalkyl, which optionally is substituted in one or more places, in the same way or differently, by halogen, $CF_3$, hydroxy, cyano, $CO_2$—($C_1$-$C_6$-alkyl), $C_1$-$C_6$-alkyl, $C_1$-$C_6$-acyl, N—($C_1$-$C_6$-alkyl)$_2$, CO—NR$^4$R$^5$ or $C_1$-$C_6$-alkoxy, R$^4$ is hydrogen, or $C_3$-$C_6$-cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_6$-$C_{12}$-aryl, which optionally is substituted in one or more places, in the same way or differently, by halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano; or $C_5$-$C_{12}$-heteroaryl, which optionally is substituted in one or more places, in the same way or differently, by halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano;

R$^5$ is hydrogen, or $C_1$-$C_6$-alkyl-$C_3$-$C_6$cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the way or differently, by $C_1$-$C_6$-alkyl, $C_1$-$C_6$-acyl, $C_1$-$C_6$-alkoxy or $CF_3$;

$C_6$-$C_{12}$-aryl, which optionally is substituted in one or more places, in the same way or differently, by halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano; or $C_5$-$C_{12}$-heteroaryl, which optionally is substituted in one or more places, in the same way or differently, by halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano;

R$^4$ and R$^5$ together can also form a 5- to 8-membered ring, which can contain additional heteroatoms, and X is sulfonyl, $(CH_2)_n$ or carbonyl, Y is —$(CH_2)_n$— or —CH=CH—, and n is 1-4.

19. A compound according to claim 1, wherein

R$^4$ is hydrogen, or $C_3$-$C_6$-cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_6$-$C_{12}$-aryl, which optionally is substituted in one or more places, in the same way or differently, by halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano;

$C_5$-$C_{12}$-heteroaryl, which optionally is substituted in one or more places, in the same way or differently, by halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano; or $C_1$-$C_6$-alkyl, R$^5$ is hydrogen, or $C_1$-$C_6$-alkyl-$C_3$-$C_6$-cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_6$-$C_{12}$-aryl, which optionally is substituted in one or more places, in the same way or differently, by halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano;

$C_5$-$C_{12}$-heteroaryl, which optionally is substituted in one or more places, in the same way or differently, by halogen, $C_1$-$C_6$-alkyl, $C_1$-$C_6$-acyl, $C_1$-$C_6$-alkoxy, N—$C_1$-$C_6$-alkyl-$C_1$-$C_6$-alkyl, $CF_3$ or cyano; or $C_1$-$C_6$-alkyl, or R$^4$ and R$^5$ together can also form a 5- to 8-membered ring, which can contain additional heteroatoms.

20. A compound according to claim 2, wherein

R$^4$ is hydrogen, $C_3$-$C_6$-cycloalkyl, which optionally is substituted in one or more places, in the same way or differently, by $C_1$-$C_3$-alkyl, $C_1$-$C_3$-acyl, $C_1$-$C_3$-alkoxy or $CF_3$;

$C_6$-$C_{12}$-aryl, which optionally is substituted in one or morn places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano;

$C_5$-$C_{12}$-heteroaryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, R$^5$ is hydrogen, or $C_1$-$C_6$-alkyl-$C_3$-$C_6$-cycloalkyl, which optionally is substituted in one or more places, in the same way or differently, by $C_1$-$C_3$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, by $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano;

$C_5$-$C_{12}$-heteroaryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl, or R$^4$ and R$^5$ together can also form a 5- to 8-membered ring, which can contain additional heteroatoms.

21. A compound according to claim 3, wherein

R$^5$ is hydrogen, $C_1$-$C_6$-alkyl-$C_3$-$C_6$-cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, by $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano;

$C_5$-$C_{12}$-heteroaryl, which optionally is substituted in one or more places, in the same way or differently, with halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl.

22. A compound according to claim 4, wherein $R^5$ is hydrogen, or $C_1$-$C_6$-alkyl-$C_3$-$C_6$-cycloalkyl, which optionally is substituted in one or more places, in the same way or differently, by $C_1$-$C_6$-alkyl, $C_1$-$C_6$-acyl, $C_1$-$C_6$-alkoxy or $CF_3$;

$C_3$-$C_6$-cycloalkyl, which optionally is substituted in one or more places, in the same way or differently, by $C_1$-$C_3$-alkyl, $C_1$-$C_3$-acyl, $C_1$-$C_3$-alkoxy or $CF_3$;

$C_6$-$C_{12}$-aryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano;

$C_5$-$C_{12}$-heteroaryl, which optionally is substituted in one or more places, in the same way or differently, by halogen, $C_1$-$C_3$-alkyl, $C_1$-$C_3$-acyl, $C_1$-$C_3$-alkoxy, N—$C_1$-$C_3$-alkyl-$C_1$-$C_3$-alkyl, $CF_3$ or cyano; or $C_1$-$C_6$-alkyl.

* * * * *

UNITED STATES PATENT AND TRADEMARK OFFICE
CERTIFICATE OF CORRECTION

| | | |
|---|---|---|
| PATENT NO. | : 7,449,459 B2 | Page 1 of 1 |
| APPLICATION NO. | : 11/727167 | |
| DATED | : November 11, 2008 | |
| INVENTOR(S) | : Bernd Buchmann | |

It is certified that error appears in the above-identified patent and that said Letters Patent is hereby corrected as shown below:

On the Title page, Foreign Application Priority Data, reads "Mar. 23, 2007" should read -- Mar. 23, 2006 --
Column 27, line 54, reads "the Same way" should read -- the same way --
Column 31, line 39, replace the period with a comma
Column 32, line 50, replace the period with a comma
Column 34, lines 41-42, reads "azoinyl," should read -- azocinyl, --
Column 34, lines 43-44, reads "cinnnnolinyl," should read -- cinnolinyl, --
Column 35, line 65, reads "morn places," should read -- more places, --
Column 36, line 16, reads "morn places," should read -- more places, --

Signed and Sealed this

Third Day of November, 2009

David J. Kappos
*Director of the United States Patent and Trademark Office*